United States Patent
Medoff et al.

(10) Patent No.: US 10,611,997 B2
(45) Date of Patent: Apr. 7, 2020

(54) COMPOSITIONS FOR ENHANCED ENZYME PRODUCTION

(71) Applicant: XYLECO, INC., Wakefield, MA (US)

(72) Inventors: Marshall Medoff, Wakefield, MA (US); Thomas Craig Masterman, Rockport, MA (US); Aiichiro Yoshida, Canton, MA (US); Jaewoong Moon, Andover, MA (US); Christopher G. Bergeron, Fitchburg, MA (US); James J. Lynch, Woburn, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 15/031,439

(22) PCT Filed: Mar. 30, 2016

(86) PCT No.: PCT/US2016/024966
§ 371 (c)(1),
(2) Date: Apr. 22, 2016

(87) PCT Pub. No.: WO2016/160956
PCT Pub. Date: Oct. 6, 2016

(65) Prior Publication Data
US 2018/0010088 A1 Jan. 11, 2018

Related U.S. Application Data

(60) Provisional application No. 62/140,785, filed on Mar. 31, 2015.

(51) Int. Cl.
| | | |
|---|---|---|
| C12N 1/14 | (2006.01) | |
| C12N 1/38 | (2006.01) | |
| C12N 1/22 | (2006.01) | |
| C12N 9/42 | (2006.01) | |
| C12P 19/02 | (2006.01) | |
| C12P 19/14 | (2006.01) | |

(52) U.S. Cl.
CPC ............... *C12N 1/14* (2013.01); *C12N 1/22* (2013.01); *C12N 1/38* (2013.01); *C12N 9/2437* (2013.01); *C12P 19/02* (2013.01); *C12P 19/14* (2013.01); *C12Y 302/01004* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 2010/0129880 A1 | 5/2010 | Gudynaite-Savitch et al. |
| 2011/0207913 A1 | 8/2011 | England et al. |
| 2012/0201947 A1 | 8/2012 | Stuart |
| 2013/0344555 A1 | 12/2013 | Angelidaki et al. |
| 2014/0011258 A1 | 1/2014 | Medoff et al. |

FOREIGN PATENT DOCUMENTS

| | | |
|---|---|---|
| CN | 104630186 A | 5/2015 |
| KR | 2013-0113006 | 10/2013 |
| WO | 2009/026716 A1 | 3/2009 |
| WO | 2014176508 A2 | 10/2014 |
| WO | 2016160956 A1 | 10/2016 |

OTHER PUBLICATIONS

Beta-D-glucoside glucohydrolase precursor. Genbank Q12175. Nov. 28, 2006. p. 1-2 (Year: 2006).*
GenBank: ETS03194. Beta-D-glucoside glucohydrolase. 2014. p. 1-2 (Year: 2014).*
International Search Report and Written Opinion from corresponding International Application No. PCT/US16/24966 dated Jun. 30, 2016.
Search Report and Written Opinion from Application SG 11201707406V dated Sep. 10, 2018.
Gritzali et al, "Relationships Between Purified Extracellular Enzymes from Induced or Cellulose-Grown Cells" America Chemical Society, 1979, pp. 237-260.
Sternberg et al, "Induction of Cellulotytic Enzymes in Trichderma reesi by Sophorose" Journal of Bacteriology, 1979, vol. 139, No. 3, pp. 761-769.
Extended European Search Report from Application EP16774087.7 dated Jan. 15, 2019.
Partial European Search Report from EP16774087.7 dated Oct. 1, 2018.

* cited by examiner

Primary Examiner — Paul J Holland
(74) Attorney, Agent, or Firm — Lando & Anastasi, LLP

(57) ABSTRACT

The present invention relates to compositions to induce production of proteins, e.g., enzymes, e.g., amylases or biomass degrading enzymes in a host cell, and methods for increasing the yield of the proteins, e.g., enzymes produced. Such compositions comprise a caramelized sugar product. The methods described herein can also be used to enhance processing of biomass materials, e.g., to produce sugar products.

21 Claims, 4 Drawing Sheets
Specification includes a Sequence Listing.

COMPOSITIONS FOR ENHANCED ENZYME PRODUCTION

RELATED APPLICATIONS

This application is a national stage application under 35 U.S.C. § 371 of International Application No. PCT/US2016/024966, filed Mar. 30, 2016, which claims priority to U.S. Provisional Application No. 62/140,785, filed Mar. 31, 2015. The entire contents of each of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Mar. 17, 2016, is named X2002-7002WO_SL.txt and is 63,369 bytes in size.

FIELD OF THE INVENTION

The present invention relates generally to compositions for enhanced production of a protein, e.g., an enzyme, e.g., an amylase or a biomass degrading enzyme, e.g., a cellulase or a hemicellulase, and methods for enhanced biomass degrading enzyme production. Such compositions comprise a caramelized sugar product. The methods described herein can be used to process biomass materials.

BACKGROUND OF THE INVENTION

Biomass degrading enzymes, such as cellulases, xylanases, and ligninases, are important for the degradation of biomass, such as feedstock. Cellulosic and lignocellulosic materials are produced, processed, and used in large quantities in a number of applications. Often such materials are used once, and then discarded as waste, or are simply considered to be wasted materials, e.g., sewage, bagasse, sawdust, and stover. Microorganisms that produce biomass degrading enzymes, endogenously or heterologously, can be used to process biomass materials, e.g., to produce sugar products. However, there exists a need for compositions and/or methods that enhance biomass degrading enzyme production to increase the efficiency of biomass processing.

SUMMARY OF THE INVENTION

The present invention is based, at least in part, on the surprising discovery that caramelized sugar products can induce production of biomass degrading enzymes when introduced to microorganisms capable of producing a biomass degrading enzyme, e.g., *T. reesei*. In addition, the yield of biomass degrading enzymes produced was higher than that produced from conventional induction methods, e.g., using cellulose containing biomass materials, e.g., corncob. Thus, provided herein are compositions and methods for enhancing the production of a biomass degrading enzyme from a microorganism.

Accordingly, in one aspect, the present invention features a method for inducing production of a protein comprising contacting a microorganism that produces the protein with a composition comprising a caramelized sugar product under conditions sufficient for production of a protein. In embodiments, the protein is an enzyme. In some embodiments, the enzyme is an amylase or a biomass degrading enzyme.

In embodiments, the microorganism is in a cell culture. In some embodiments, sugar is added to the cell culture prior to contacting the microorganism with the composition comprising a caramelized sugar product. In some embodiments, the microorganism is contacted with the composition comprising a caramelized sugar product when the cell culture is substantially free from sugar.

In embodiments, the caramelized sugar product is produced by caramelizing glucose, xylose, maltose, lactose, or a combination thereof. In some embodiments, the caramelized sugar product is produced by caramelizing saccharified biomass comprising xylose and glucose. In some embodiments, the caramelized sugar product comprises oligosaccharides, dehydration products of the oligosaccharides, hydration products of the oligosaccharides, disproportionation products of the oligosaccharides, colored aromatic products, or any combination thereof. In some embodiments, the oligosaccharides comprise disaccharides, trisaccharides, tetrasaccharides, pentasaccharides, hexasaccharides, or a combination thereof. In one embodiment, the caramelized sugar product is produced by caramelizing glucose and the oligosaccharides comprise disaccharides, trisaccharides, tetrasaccharides, pentasaccharides, hexasaccharides, or a combination thereof, comprising glucose. In one embodiment, the caramelized sugar product is produced by caramelizing maltose and the oligosaccharides comprise disaccharides, trisaccharides, tetrasaccharides, pentasaccharides, hexasaccharides, or a combination thereof, comprising maltose. In one embodiment, the caramelized sugar product is produced by caramelizing lactose and the oligosaccharides comprise disaccharides, trisaccharides, tetrasaccharides, pentasaccharides, hexasaccharides, or a combination thereof, comprising lactose. In one embodiment, the caramelized sugar product is produced by caramelizing xylose and the oligosaccharides comprise disaccharides, trisaccharides, tetrasaccharides, pentasaccharides, hexasaccharides, or a combination thereof, comprising xylose. In some embodiments, when the oligosaccharides comprise more than one species of oligosaccharides, trisaccharides are the most abundant species.

In some embodiments, the biomass degrading enzyme comprises an amylase, e.g., an alpha, beta or gamma amylase, an endoglucanase, an exoglucanase, a cellobiase, a cellobiohydrolase, a xylanase, a ligninase, or a hemicellulase, or a combination thereof.

In some embodiments, the composition further comprises an inducer biomass. In some embodiments, the inducer biomass comprises a starchy material or a starchy material that includes a cellulosic component. In some embodiments, the inducer biomass, e.g., starchy material or starchy material that includes a cellulosic component, comprises one or more of an agricultural product or waste, a paper product or waste, a forestry product, or a general waste, or any combination thereof. In some embodiments, the agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof. In some embodiments, the agricultural product or waste comprises corn cobs, corn stover, corn fiber, or beeswing. In some embodiments, the agricultural product or waste comprises corn cobs. In some embodiments, the agricultural product or waste comprises beeswing. In some embodiments, the paper product or waste comprises paper, pigmented papers, loaded papers, coated papers, filled papers, magazines, printed matter, printer paper, polycoated paper, cardstock, cardboard, paperboard, or paper pulp, or a combination thereof. In some embodiments, the forestry product comprises aspen wood, particle board, wood chips, or sawdust, or a combination thereof. In some embodiments, the general waste comprises manure, sewage, or offal, or a combination thereof.

In some embodiments, the inducer biomass is pre-treated to reduce the recalcitrance of the inducer biomass. In some embodiments, the pre-treatment of the inducer biomass comprises exposure to an electron beam, bombardment with electrons, sonication, oxidation, pyrolysis, steam explosion, chemical treatment, mechanical treatment, or freeze grinding. In some embodiments, the pre-treatment of the inducer biomass comprises exposure to an electron beam or bombardment with electrons.

In one embodiment, the composition further comprises cellobiose, β-cellobiono-1,5-lactone, lactose, D-xylose, xylobiose, galactose, and sophorose.

In some embodiments, the microorganism that produces a biomass degrading enzyme is from a species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*. In some embodiments, the microorganism is a fungal cell. In some embodiments, the microorganism that produces a biomass degrading enzyme is selected from *Aspergillus, Humicola insolens (Scytalidium thermophilum), Coprinus cinereus, Fusarium oxysporum, Myceliophthora thermophila, Meripilus giganteus, Thielavia terrestris, Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, Acremonium furatum, Chrysosporium lucknowense, Trichoderma viride, Trichoderma reesei*, or *Trichoderma koningii*. In some embodiments, the microorganism is *T. reesei*. In certain embodiments, the microorganism is *T. reesei*, or a variant thereof, e.g., RUT-NG14, PC3-7, QM9414, and RUT-C30.

In some embodiments, the amount of biomass degrading enzyme produced is increased by at least 1-fold, e.g., at least 1.2-fold, 1.5-fold, 1.8-fold, 2-fold, or more, compared the amount of biomass degrading enzyme produced by the microorganism without contacting with a caramelized sugar product. In some embodiments, the amount of biomass degrading enzyme produced is increased by at least 1-fold, e.g., at least 1.2-fold, 1.5 fold, 1.8-fold, 2-fold, compared the amount of biomass degrading enzyme produced by contacting the microorganism with a inducer biomass. In some embodiments, the biomass degrading enzyme comprises one or more, or all, of the enzymes listed in Table 1.

In some embodiments, the method further comprises separating the biomass degrading enzyme from a component of the cell culture. In some embodiments, the method further comprises separating the biomass degrading enzyme from the microorganism or remaining inducer biomass. In some embodiments, the method further comprises separating the biomass degrading enzyme from the microorganism or remaining inducer biomass by chromatography or filtration. In some embodiments, the biomass degrading enzyme is purified from the cell culture.

In some embodiments, the method further comprises a step comprising: a) contacting the microorganism with a sugar in a first container under conditions such that the microorganism proliferates; and b) transferring the microorganism to a second container, wherein the second container is larger, e.g., by volume, than the first container; and wherein said step is performed prior to contacting the microorganism with the composition. In some embodiments, the step is repeated 1 or more times, e.g., 2, 3, 4, 5 times.

In another aspect, the present invention features a method for producing a product from a biomass, comprising: a) inducing the production of a biomass degrading enzyme using a method comprising contacting a microorganism that produces the biomass degrading enzyme with a composition comprising a caramelized sugar product under conditions sufficient for production of a biomass degrading enzyme; b) providing a biomass; and c) contacting the biomass with the microorganism of step a) or the biomass degrading enzyme that has been separated or purified from the microorganism of step a), under conditions suitable for production of the product. In some embodiments, the product is a sugar product. In some embodiments, the product is glucose and/or xylose. In some embodiments, the method further comprises isolating the product. In some embodiments, the isolating of the product comprises precipitation, crystallization, chromatography, centrifugation, and/or extraction.

In some embodiments, the biomass degrading enzyme is an endoglucanase, a cellobiase, a cellobiohydrolase, a xylanase, a ligninase, or a hemicellulase, or a combination thereof. In some embodiments, the biomass degrading enzyme comprises one or more, or all, of the enzymes listed in Table 1.

In some embodiments, the method further comprises a step of treating the biomass prior to step c) to reduce the recalcitrance of the biomass. In some embodiments, the treating comprises exposure to an electron beam, bombardment with electrons, sonication, oxidation, pyrolysis, steam explosion, chemical treatment, mechanical treatment, or freeze-grinding. In some embodiments, the treating comprises exposure to an electron beam or bombardment with electrons.

In some embodiments, the biomass comprises a starchy material or a starchy material that includes a cellulosic component. In some embodiments, the biomass comprises one or more of an agricultural product or waste, a paper product or waste, a forestry product, or a general waste, or any combination thereof; wherein: a) an agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof; b) a paper product or waste comprises paper, pigmented papers, loaded papers, coated papers, filled papers, magazines, printed matter, printer paper, polycoated paper, cardstock, cardboard, paperboard, or paper pulp, or a combination thereof; c) a forestry product comprises aspen wood, particle board, wood chips, or sawdust, or a combination thereof; and d) a general waste comprises manure, sewage, or offal, or a combination thereof.

In some embodiments, the caramelized sugar product is produced by caramelizing glucose, maltose, xylose, lactose, or a combination thereof. In some embodiments, the caramelized sugar product is produced by caramelizing saccharified biomass comprising xylose and glucose. In some embodiments, the caramelized sugar product comprises oligosaccharides, dehydration products of the oligosaccharides, hydration products of the oligosaccharides, disproportionation products of the oligosaccharides, colored aromatic products, or any combination thereof. In some embodiments, the oligosaccharides comprise disaccharides, trisaccharides, tetrasaccharides, pentasacchrides, hexasaccharides, or a combination thereof. In some embodiments, the caramelized sugar product is produced by caramelizing glucose and the oligosaccharides comprise disaccharides, trisaccharides, tetrasaccharides, pentasaccharides, hexasaccharides, or a combination thereof, comprising glucose. In some embodiments, the caramelized sugar product is produced by caramelizing maltose and the oligosaccharides comprise disaccharides, trisaccharides, tetrasaccharides, pentasaccharides, hexasaccharides, or a combination thereof, comprising maltose. In some embodiments, the caramelized sugar product is produced by caramelizing lactose and the oligosaccharides comprise disaccharides, trisaccharides, tetrasaccharides, pentasaccharides, hexasaccharides, or a combination thereof, comprising lactose. In some embodiments, the caramelized sugar product is produced by caramelizing xylose and wherein the oligosaccharides comprise disaccharides, trisaccharides, tetrasaccharides, pentasaccharides, hexasaccharides, or a combination thereof, comprising xylose. In some embodiments, when the oligosaccharides comprise more than one species of oligosaccharides, trisaccharides are the most abundant species.

In some embodiments, the composition further comprises an inducer biomass. In some embodiments, the inducer biomass comprises a starchy material or a starchy material that includes a cellulosic component. In some embodiments, the inducer biomass comprises one or more of an agricultural product or waste, a paper product or waste, a forestry product, or a general waste, or any combination thereof; wherein a) an agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof; b) a paper product or waste comprises paper, pigmented papers, loaded papers, coated papers, filled papers, magazines, printed matter, printer paper, polycoated paper, cardstock, cardboard, paperboard, or paper pulp, or a combination thereof; c) a forestry product comprises aspen wood, particle board, wood chips, or sawdust, or a combination thereof; and d) a general waste comprises manure, sewage, or offal, or a combination thereof.

In some embodiments, the inducer biomass is pre-treated to reduce the recalcitrance of the inducer biomass. In some embodiments, the pre-treatment of the biomass comprises exposure to an electron beam, bombardment with electrons, sonication, oxidation, pyrolysis, steam explosion, chemical treatment, mechanical treatment, or freeze grinding. In some embodiments, the pre-treatment of the biomass comprises exposure to an electron beam or bombardment with electrons. In some embodiments, the inducer biomass of the present invention is the same as the biomass provided in step (b).

In one embodiment, the composition further comprises cellobiose, β-cellobiono-1,5-lactone, lactose, D-xylose, xylobiose, galactose, and sophorose.

In some embodiments, the microorganism that produces a biomass degrading enzyme is from a species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*. In some embodiments, the microorganism is a fungal cell. In some embodiments, the microorganism that produces a biomass degrading enzyme is selected from *Aspergillus, Humicola insolens (Scytalidium thermophilum), Coprinus cinereus, Fusarium oxysporum, Myceliophthora thermophila, Meripilus giganteus, Thielavia terrestris, Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, Acremonium furatum, Chrysosporium lucknowense, Trichoderma viride, Trichoderma reesei,* or *Trichoderma koningii*. In some embodiments, the microorganism is *T. reesei*. In certain embodiments, the microorganism is *T. reesei*, or a variant thereof, e.g., RUT-NG14, PC3-7, QM9414, and RUT-C30.

In yet another aspect, the present invention features a composition comprising a caramelized sugar product for use in the methods disclosed herein. In some embodiments, the caramelized sugar product is produced by caramelizing glucose, maltose, xylose, lactose, or a combination thereof. In some embodiments, the caramelized sugar product is produced by caramelizing saccharified biomass comprising xylose and glucose. In some embodiments, the caramelized sugar product comprises oligosaccharides, dehydration products of the oligosaccharides, hydration products of the oligosaccharides, disproportionation products of the oligosaccharides, colored aromatic products, or any combination thereof. In some embodiments, the oligosaccharides comprise disaccharides, trisaccharides, tetrasaccharides, pentasacchrides, hexasaccharides, or a combination thereof. In some embodiments, the caramelized sugar product is produced by caramelizing glucose and the oligosaccharides comprise disaccharides, trisaccharides, tetrasaccharides, pentasaccharides, hexasaccharides, or a combination thereof, comprising glucose. In some embodiments, the caramelized sugar product is produced by caramelizing maltose and the oligosaccharides comprise disaccharides, trisaccharides, tetrasaccharides, pentasaccharides, hexasaccharides, or a combination thereof, comprising maltose. In some embodiments, the caramelized sugar product is produced by caramelizing lactose and the oligosaccharides comprise disaccharides, trisaccharides, tetrasaccharides, pentasaccharides, hexasaccharides, or a combination thereof, comprising lactose. In some embodiments, the caramelized sugar product is produced by caramelizing xylose and the oligosaccharides comprise disaccharides, trisaccharides, tetrasaccharides, pentasaccharides, hexasaccharides, or a combination thereof, comprising xylose. In some embodiments, when the oligosaccharides comprise more than one species of oligosaccharides, trisaccharides are the most abundant species.

In some embodiments, the composition further comprises an inducer biomass. In some embodiments, the inducer biomass comprises a starchy material or a starchy material that includes a cellulosic component. In some embodiments, the inducer biomass comprises one or more of an agricultural product or waste, a paper product or waste, a forestry product, or a general waste, or any combination thereof. An agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof. A paper product or waste comprises paper, pigmented papers, loaded papers, coated papers, filled papers, magazines, printed matter, printer paper, polycoated paper, cardstock, cardboard, paperboard, or paper pulp, or a combination thereof. A forestry product comprises aspen wood, particle board, wood chips, or sawdust, or a combination thereof. A general waste comprises manure, sewage, or offal, or a combination thereof.

In some embodiments, the inducer biomass is pre-treated to reduce the recalcitrance of the inducer biomass. In some embodiments, the pre-treatment of the biomass comprises exposure to an electron beam, bombardment with electrons, sonication, oxidation, pyrolysis, steam explosion, chemical treatment, mechanical treatment, or freeze grinding. In some embodiments, the pre-treatment of the biomass comprises exposure to an electron beam or bombardment with electrons.

In one embodiment, the composition further comprises cellobiose, β-cellobiono-1,5-lactone, lactose, D-xylose, xylobiose, galactose, and sophorose.

In still another aspect, the present invention features a cell culture comprising a microorganism capable of producing a biomass degrading enzyme and a caramelized sugar product. In some embodiments, the cell culture further comprises cell culture media. In some embodiments, the biomass degrading enzyme is an endoglucanase, a cellobiase, a cellobiohydrolase, a xylanase, a ligninase, or a hemicellulase, or a combination thereof. In some embodiments, the biomass degrading enzyme comprises one or more, or all, of the enzymes listed in Table 1. In some embodiments, the caramelized sugar product is produced by caramelizing glucose, maltose, xylose, lactose, or a combination thereof. In some embodiments, the caramelized sugar product is produced by caramelizing saccharified biomass comprising xylose and glucose. In some embodiments, the oligosaccharides comprise disaccharides, trisaccharides, tetrasaccharides, pentasacchrides, hexasaccharides, or a combination thereof. In some embodiments, the caramelized sugar product comprises oligosaccharides, dehydration products of the oligosaccharides, hydration products of the oligosaccharides, disproportionation products of the oligosaccharides, colored aromatic products, or any combination thereof. In some embodiments, the caramelized sugar product is produced by caramelizing glucose and the oligosaccharides comprise disaccharides, trisaccharides, tetrasaccharides, pentasaccharides, hexasaccharides, or a combination thereof, comprising glucose. In some embodiments, the caramelized sugar product is produced by caramelizing maltose and the oligosaccharides comprise disaccharides, trisaccharides, tetrasaccharides, pentasaccharides, hexasaccharides, or a combination thereof, comprising maltose. In some embodiments, the caramelized sugar product is produced by caramelizing lactose and the oligosaccharides comprise disaccharides, trisaccharides, tetrasaccharides, pentasaccharides, hexasaccharides, or a combination thereof, comprising lactose. In some embodiments, the caramelized sugar product is produced by caramelizing xylose and the oligosaccharides comprise disaccharides, trisaccharides, tetrasaccharides, pentasaccharides, hexasaccharides, or a combination thereof, comprising xylose.

In some embodiments, the microorganism is from a species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*. In some embodiments, the microorganism is a fungal cell. In some embodiments, the microorganism is selected from *Aspergillus, Humicola insolens (Scytalidium thermophilum), Coprinus cinereus, Fusarium oxysporum, Myceliophthora thermophila, Meripilus giganteus, Thielavia terrestris, Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, Acremonium furatum, Chrysosporium lucknowense, Trichoderma viride, Trichoderma reesei,* or *Trichoderma koningii*. In some embodiments, the microorganism is *T. reesei*. In certain embodiments, the microorganism is *T. reesei*, or a variant thereof, e.g., RUT-NG14, PC3-7, QM9414, and RUT-C30.

In some embodiments, the cell culture further comprises an inducer biomass. In some embodiments, the inducer biomass comprises a starchy material or a starchy material that includes a cellulosic component. In some embodiments, the inducer biomass comprises one or more of an agricultural product or waste, a paper product or waste, a forestry product, or a general waste, or any combination thereof; wherein a) an agricultural product or waste comprises sugar cane jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof; b) a paper product or waste comprises paper, pigmented papers, loaded papers, coated papers, filled papers, magazines, printed matter, printer paper, polycoated paper, cardstock, cardboard, paperboard, or paper pulp, or a combination thereof; c) a forestry product comprises aspen wood, particle board, wood chips, or sawdust, or a combination thereof; and d) a general waste comprises manure, sewage, or offal, or a combination thereof.

In some embodiments, the cell culture further comprises a biomass degrading enzyme produced by the microorganism. In some embodiments, the biomass degrading enzyme is an endoglucanase, a cellobiase, a cellobiohydrolase, a xylanase, a ligninase, or a hemicellulase, or a combination thereof. In some embodiments, the biomass degrading enzyme comprises one or more, or all, of the enzymes listed in Table 1.

DETAILED DESCRIPTION

Definitions

Figure 1:
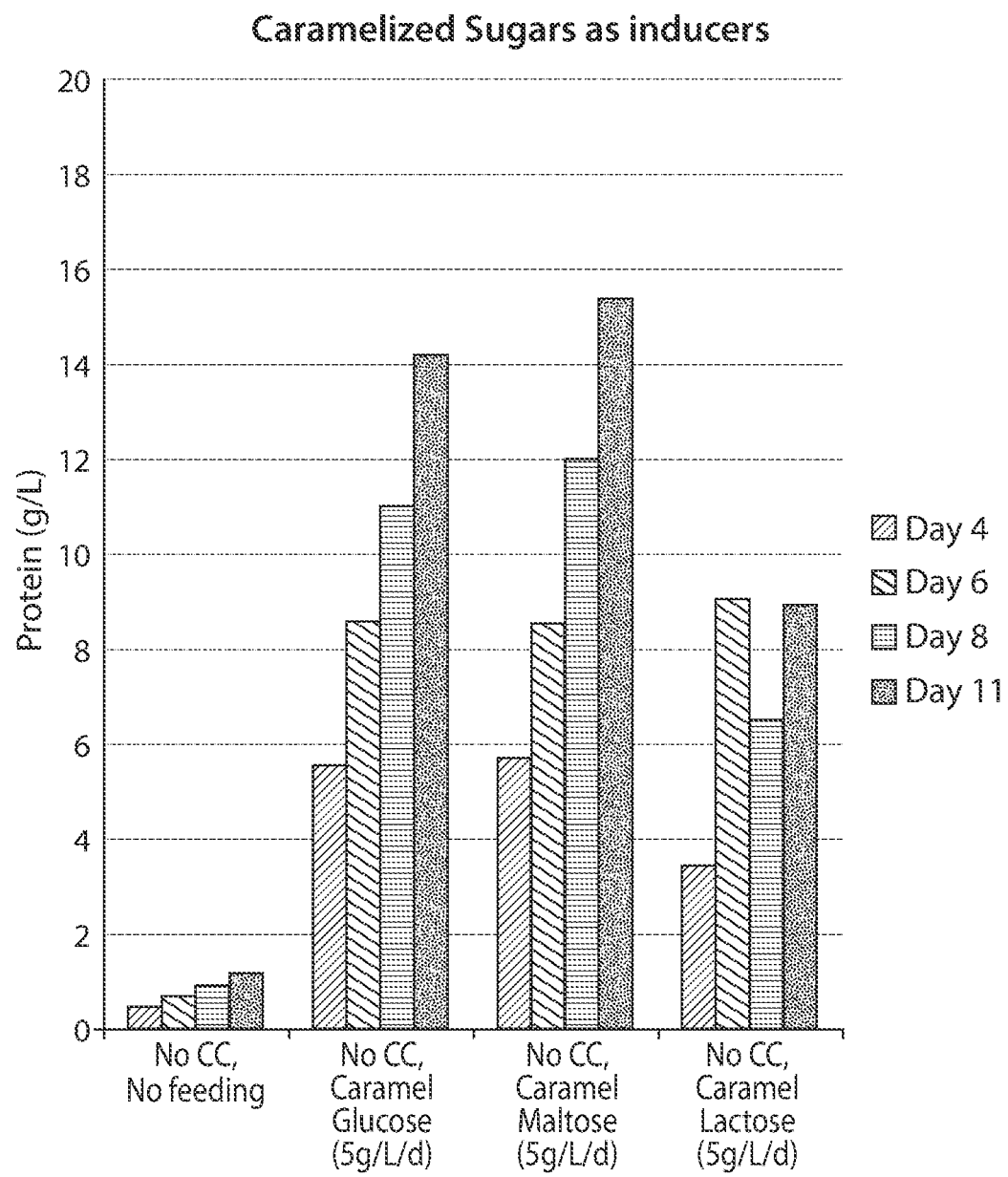
FIG. 1 is a graph showing the induction of cellulase production by caramelized sugars without cellulose inducer corncob (No CC). Caramelized glucose, caramelized maltose, caramelized lactose or no caramelized sugar (no feeding) was fed to cultures of *T. reesei* at 5 g/L/day. Cellulase production was measured by protein titer (g/L) at days 4, 6, 8 and 11, and represented on the y-axis.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "biomass", as used herein, refers to any non-fossilized, organic matter. Biomass can be a starchy material and/or a cellulosic, hemicellulosic, or lignocellulosic material. For example, the biomass can be an agricultural product, a paper product, forestry product, or any intermediate, byproduct, residue or waste thereof, or a general waste. The biomass may be a combination of such materials. In an embodiment, the biomass is processed, e.g., by a saccharification and/or a fermentation reaction described herein, to produce products, such as sugars, alcohols, organic acids, or biofuels.

The term "biomass degrading enzyme", as used herein, refers to an enzyme that breaks down components of the biomass matter described herein into intermediates or final products. For example, a biomass degrading enzyme includes at least amylases, e.g., alpha, beta or gamma amylases, cellulases, hemicellulases, ligninases, endoglucancases, cellobiases, xylanases, and cellobiohydrolases. Biomass degrading enzymes are produced by a wide variety of microorganisms, and can be isolated from the microorganisms, such as *T. reesei*. The biomass degrading enzyme can be endogenously expressed or heterologously expressed.

The term "biomass degrading activity", as used herein, refers to enzymatic activity that breaks down components of the biomass matter described herein into intermediates or final products. Biomass degrading activity includes at least cellulase activity, hemicellulase activity, ligninase activity, endoglucanase activity, cellobiase activity, cellobiohydrolase activity, and xylanase activity.

The term "caramelized sugar product", as used herein, refers to a small molecule or compound, or a mixture thereof, that is produced from heating (with or without a solvent, such as water present) a sugar molecule, e.g., to at least 110° C., to cause browning of the sugar. Sugar molecules suitable for producing caramelized sugar products include, for example, glucose, xylose, maltose, lactose, fructose, sucrose, sugar blends from saccharified biomass, such as saccharified corn cob, or any combination thereof. A caramelized sugar product may comprise oligosaccharides, e.g., oligosaccharides of the sugar molecule starting material, dehydration products of the oligosaccharides, hydration products of the oligosaccharides, disproportionation products of the oligosaccharides, colored aromatic products, or any combination thereof.

The term "cellobiase", as used herein, refers to an enzyme that catalyzes the hydrolysis of a dimer, trimer, tetramer, pentamer, hexamer, heptamer, octamer, or an oligomer of glucose, or an oligomer of glucose and xylose, to glucose and/or xylose. For example, the cellobiase is beta-glucosidase, which catalyzes beta-1,4 bonds in cellobiose to release two glucose molecules.

The term "cellobiohydrolase" as used herein, refers to an enzyme that hydrolyzes glycosidic bonds in cellulose. For example, the cellobiohydrolase is 1,4-beta-D-glucan cellobiohydrolase, which catalyzes the hydrolysis of 1,4-beta-D-glucosidic linkages, e.g., 1,4-beta-D-glucosidic linkages of the terminal units, in cellulose, cellulooligosaccharides, or any beta-1,4-linked glucose containing polymer, releasing oligosaccharides from the polymer chain.

The term "cellulase", as used herein, refers to an enzyme that catalyzes the break down, e.g., hydrolysis, of cellulose and related polysaccharides into shorter polysaccharides, oligosaccharides, or monosaccharides. Examples of cellulases include endoglucanases, cellobiases, and cellobiohydrolases (or exoglucanases). Cellulase activity refers to the activity of a cellulose, e.g., cellulolysis, and can include the hydrolysis of the 1,4-beta-D-glycosidic linkages in cellulose, hemicelluloses, lichenin, and cereal beta-D-glucans into shorter polysaccharides, oligosaccharides, or monosaccharides.

The term "endoglucanase" as used herein, refers to an enzyme that catalyzes the hydrolysis of internal β-1,4 glycosidic bonds. For example, the endoglucanase is endo-1, 4-(1,3; 1,4)-beta-D-glucan 4-glucanohydrolase, which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1, 3 glucans such as cereal beta-D-glucans or xyloglucans, and other plant material containing cellulosic components.

The term "inducer biomass", as used herein, refers to any non-fossilized, organic matter that is introduced to a microorganism to induce the production of a protein, such as an enzyme, such as a biomass degrading enzyme. The inducer biomass can be a starchy material and/or a cellulosic material comprising cellulose. The inducer biomass can also be referred to as a cellulose inducer. The inducer biomass can comprise the same component(s) as a biomass that is used for production of a sugar product. In an embodiment, the inducer biomass can be introduced with a caramelized sugar product to induce production of a biomass degrading enzyme.

The term "ligninase", as used herein, refers to an enzyme that catalyzes the breakdown of lignin, commonly found in the cell walls of plants, such as by an oxidation reaction. Ligninases include lignin-modifying enzymes, lignin peroxidases and laccases.

The terms "nucleic acid" or "polynucleotide" are used interchangeable, and refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof. A "plurality of polypeptides" refers to two or more polypeptides, e.g., 2, 3, 4, 5, 6, 7, 8, 9, 10, 20, 50, 100, 200, or 500 or more polypeptides.

The term "xylanase" as used herein, refers to enzymes that hydrolyze xylan-containing material. Xylan is polysaccharide comprising units of xylose. A xylanase can be an endoxylanase, a beta-xylosidase, an arabinofuranosidase, an alpha-glucuronidase, an acetylxylan esterase, a feruloyl esterase, or an alpha-glucuronyl esterase.

Description

Materials comprising cellulose or hemicellulose, e.g., corncob, wheat straw, sawdust, etc., can be used for production of cellulases and hemicellulases in the filamentous fungus, *Trichoderma reesei* (*T. reesei*) (Lynd et al., 2002, Microbiol & Mol Biol Rev, 66:506-577). Sugars, such as glucose, xylose and fructose, are typically regarded as a soluble carbon source for *T. reesei*. Some studies have shown that the presence of easily metabolisable carbon sources such as glucose and fructose, represses the expression of cellulolytic genes (Chambergo et al., 2002, J Biol Chem. 7:1383-13988).

The present invention is based, at least in part, on the surprising discovery that caramelized sugar products produced by heating sugar molecules, e.g., glucose and/or xylose, can induce production of proteins, e.g., enzymes, e.g., amylases or biomass degrading enzymes when introduced to microorganisms, e.g., *T. reesei*. Furthermore, the yield of proteins, e.g., biomass degrading enzymes produced was higher than that produced from conventional induction methods, e.g., using a cellulose-containing inducer, e.g., corncob. Accordingly, the present invention provides compositions comprising a caramelized sugar product for inducing production of proteins, e.g., enzymes, e.g., amylases or biomass degrading enzymes in a microorganism, and methods of use thereof.

Caramelized Sugar Product

In embodiments, a composition comprising a caramelized sugar product is introduced to a microorganism e.g., to induce production of a biomass degrading enzyme. Caramelization is a non-enzymatic process commonly used in cooking by which sugar molecules are heated to a sufficient temperature to brown the sugar and produce a caramel. Generally, the sugar can be a 3, 4, 5, 6, or 7-carbon carbohydrate, e.g., glyceraldehyde, dihidroxyacetone, erythrose, threose, arabinose, ribose, ribulose, xylose, xylulose, lyxose, allose, altrose, fructose, galactose, glucose, gulose, idose, mannose, sorbose, talose, tagatose, sedoheptulose and mannoheptulose or mixtures of any of these. For example, suitable sugar molecules that can be used as the starting material for caramelization include glucose, maltose, lactose, xylose, fructose, and sucrose. In an embodiment, glucose is caramelized. In an embodiment, maltose is caramelized. In an embodiment, lactose is caramelized. In an embodiment, xylose is caramelized. In an embodiment, sugars from saccharified biomass, e.g., saccharified corn cob, wheat straw and/or a starchy material are caramelized. Any combination of glucose, maltose, lactose, xylose, fructose, and/or sucrose can be caramelized. For example, in one embodiment, a mixture comprising xylose and glucose is caramelized.

Sugar molecules are caramelized by heating to a sufficient temperature to brown the sugar. In embodiments, the sugar molecules are heated to at least 110° C., 120° C., 130° C., 140° C., 150° C., 160° C., 170° C., 180° C., 190° C., or 200° C. The temperature used can depend on the sugar starting material, as different sugar molecules can be caramelized at different temperatures, e.g., fructose caramelizes at 110° C. while glucose caramelizes at 160° C. The sugar molecules can be heated at a caramelization temperature described herein for a duration of time until a desired level of caramelization is achieved. For example, the sugar molecules are heated at a caramelization temperature described herein for at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, or 48 hours. For example, sugar molecules can be caramelized by heating to 170° C. for 17 hours. Heating can be performed by heating neat sugars, e.g., solid sugars, or sugars in solution, e.g., in water or another solvent.

The caramelization process produces a mixture of caramelized sugar products. The process includes reactions involving the oxidation of the sugar, the removal of water, and the break down of the sugar and results in hundreds of caramelized sugar products. A recent study has attempted to characterize the chemical composition of caramel, e.g., see Golon and Kuhnert, 2012, J. Agric. Food Chem., 60:3266-3274. Caramelized sugar products include one or more of: 1) oligosaccharides comprising the starting sugar molecule; 2) dehydration products of the starting sugar molecule and the oligosaccharides comprising the starting sugar molecule; 3) hydration products of the oligosaccharides comprising the starting sugar molecule; 4) fragmentation products arising from a redox disproportionation reaction of the oligosaccharides comprising the starting sugar molecule; and 5) and aromatic compounds. The caramelized sugar product utilized in the methods disclosed herein for inducing production of proteins e.g., biomass degrading enzymes in a host cell can be any of the caramelized sugar products described herein, or a combination thereof. Without wishing to be bound by theory, it is believed that oligosaccharides produced by the caramelization process plays a role in inducing the production of proteins, e.g., biomass degrading enzymes in microorganisms. It is believed that the described oligosaccharides perform two roles. First, it is believed that the oligosaccharides can partially be utilized by the organism, thus growing cell mass. Second, the oligosaccharides may trick the organism into producing enzymes so that the organism can break down the oligosaccharides to release more monosaccharides that will enhance cell growth. Enhanced cell growth gives more protein.

In an embodiment, the caramelized sugar product comprises one or more oligosaccharides comprising the starting sugar molecule, where the oligosaccharides comprise two, three, four, five, or six units of the starting sugar molecule, or a portion thereof. The oligosaccharides comprising the starting sugar molecules are formed through unselective glycosidic bond formation. For example, caramelized glucose comprises oligosaccharides comprising 2, 3, 4, 5, or 6 glucose molecules, or a combination thereof, e.g., disaccharides, trisaccharides, tetrasaccharides, pentasaccharides, or hexasaccharides comprising glucose, or a combination thereof. In another example, caramelized maltose comprises oligosaccharides comprising 2, 3, 4, 5, or 6 maltose molecules, e.g., disaccharides, trisaccharides, tetrasaccharides, pentasaccharides, or hexasaccharides comprising maltose, or a combination thereof. In another example, caramelized xylose comprises oligosaccharides comprising 2, 3, 4, 5, or 6 xylose molecules, e.g., disaccharides, trisaccharides, tetrasaccharides, pentasaccharides, or hexasaccharides comprising xylose, or a combination thereof. In yet another example, caramelized lactose comprises oligosaccharides comprising 2, 3, 4, 5, or 6 lactose molecules, or a combination thereof, e.g., disaccharides, trisaccharides, tetrasaccharides, pentasaccharides, or hexasaccharides comprising lactose repeat units, or a combination thereof.

In an embodiment, the caramelized sugar product comprises a mixture of oligosaccharides comprising the starting sugar molecules, e.g., more than one, two, three, four, or five species of oligosaccharides. In embodiments where the caramelized sugar product comprises more than one species of oligosaccharides, each species of oligosaccharides may be present at different ratios compared to the remaining oligosaccharide species. In such embodiments wherein the caramelized sugar product comprises more than one species of oligosaccharides, the trisaccharides most abundant species of oligosaccharides. In embodiments wherein the caramelized sugar product comprises disaccharides and trisaccharides, the disaccharides are the second most abundant species of oligosaccharides. In embodiments wherein the caramelized sugar product comprises disaccharides, trisaccharides, and tetrasaccharides, tetrasaccharides are the third most abundant species of oligosaccharides.

In an embodiment, the caramelized sugar product comprises one or more dehydration products of the starting sugar molecule and/or the oligosaccharides comprising the starting sugar molecule. Dehydration products can comprise the loss of 1, 2, 3, 4, 5, 6, 7, or 8 water molecules, depending on the number of monosaccharide units. Loss of water molecules may occur at the same saccharide moiety or can be distributed over two or more different saccharide moieties, e.g., of an oligosaccharide comprising the starting sugar molecule. For example, for glucose, up to 7 dehydration products can be obtained by caramelization as a result of a loss of a single water molecule.

In an embodiment, the caramelized sugar product comprises one or more hydration products of the oligosaccharides comprising the starting sugar molecule. Hydration products can comprise one or two additional water molecules added to an oligosaccharide comprising the starting sugar molecule.

In an embodiment, the caramelized sugar product comprises one or more fragmentation products, or redox disproportionation products, of the oligosaccharides comprising the starting sugar molecule. The oligosaccharides comprising the starting sugar molecule may be oxidized and/or reduced. In an embodiment, an oligosaccharide comprising the starting sugar molecule is simultaneously reduced and oxidized.

In an embodiment, the caramelized sugar product comprises one or more aromatic products. Aromatic products include aromatic dye molecules that confer the brown color of caramel. Analysis of caramelized glucose and fructose indicated that the aromatic dye molecules may differ between different starting sugar molecules (Golon et al., 2012). Aromatic products can also include the aromatic flavor molecules that confer the flavor of caramel, e.g., the "butterscotch" flavor. Examples of aromatic flavor molecules include diacetyl furans, e.g., hydroxymethylfurfural (HMF) and hydroxyacetylfuran (HAF), furanones, e.g., hydroxydimethylfuranone (HDF), dihydroxydimethylfuranone (DDF), and maltol from disaccharides and hydroxymaltol from monosaccharides.

The chemical composition of a caramelized sugar can be determined by mass spectrometry. For example, a caramelized sugar can be prepared by heating a starting sugar molecule, e.g., glucose, at 170° C. for 17 hours or 180° for 2 hours. The caramelized sugar is then dissolved in water or a mixture of methanol/water (1:1, v/v, 1 ml), and analyzed by mass spectrometry. Examples of mass spectrometry techniques that can be used to analyze the caramelized sugar samples include MALDI-TOF, micrOTOF and direct infusion ion trap mass spectrometry (ESI-TOF-MS), liquid chromatography-mass spectrometry (LC-MS or HPLC-MS), or liquid chromatography-time of flight mass spectrometry (LC-TOF or HPLC-TOF).

The composition comprising a caramelized sugar product for inducing production of a protein, e.g., a biomass degrading enzyme in a host cell or microorganism can further comprise one or more agents known in the art that can induce production of a protein, e.g., a biomass degrading enzyme. Examples of such agents include, but are not limited to, cellobiose (β-D-glucopyranosyl-(1→4)-β-D-glucopyranose), β-cellobiono-1, 5-lactone (β-D-glucopyranosyl-(1→4)-D-glucono-1,5-lactone), lactose (β-D-galactopyranosyl-(1→4)-D-glucose), sophorose (2-O-β-D-glucopyranosyl-α-D-glucose), D-xylose, xylobiose, galactose, 1-arabitol and 1-sorbose (Shmoll and Kubicek, 2003, Acta Microbiol Immunol Hung. 7:125-145; El-Gogary et al, 1989, Proc Natl Acad Sci USA, 7:6138-6141; Aro et al., 2005, FEMS Microbiol. Rev. 29:719-739; and Nogawa et al., 2001, Curr Genet. 7:329-334).

Also provided herein are compositions comprising a caramelized sugar product for inducing production of a protein, e.g., an enzyme, e.g., an amylase or biomass degrading enzyme for use in any of the methods described herein. The composition can further comprise an inducer biomass described herein, and/or additional agents known in the art that induce production of a protein, e.g., an enzyme, e.g., an amylase or biomass degrading enzyme.

In embodiments, the composition comprising a caramelized sugar product for inducing production of proteins, e.g., enzymes, e.g., amylases or biomass degrading enzymes in a host cell or microorganism may further comprise an inducer biomass described herein. In some embodiments, the inducer biomass material may be the same material that can be processed to generate various products, such as hydrogen, sugars, and alcohols. An inducer biomass can be a starchy material comprising cellulose, and is also referred to herein as a cellulose inducer. Suitable examples of inducer biomass are described further herein. The inducer biomass may be pretreated to reduce recalcitrance by any of the treatment methods described herein, e.g., exposure to an electron beam, bombardment with electrons, sonication, oxidation, pyrolysis, steam explosion, chemical treatment, mechanical treatment, and/or freeze grinding.

Use of a composition comprising a caramelized sugar product to induce production of a protein, e.g., an enzyme, e.g., an amylase or biomass degrading enzyme can result in an increase in the amount of protein, e.g., enzyme, e.g., amylase or biomass degrading enzyme produced. In an embodiment, the increase in the amount of biomass degrading enzyme produced by contacting a host cell or microorganism with a composition comprising a caramelized sugar product is at least 1 fold, 1.1 fold, 1.2 fold, 1.3 fold, 1.4 fold, 1.5 fold, 1.6 fold, 1.8 fold 1.9 fold, 2 fold, 2.1 fold, 2.2 fold, 2.3 fold, 2.4 fold, 2.5 fold, 2.6 fold, 2.7 fold, 2.8 fold, 2.9 fold, or 3 fold more, as compared to the amount of biomass degrading enzyme produced without use of a composition comprising the caramelized sugar product. In an embodiment, the amount of biomass degrading enzyme produced by contacting a host cell or microorganism with a composition comprising a caramelized sugar product is at least 1%, 2%, 5%, 10%, 25%, 50%, 75%, 100%, 200%, 300%, 400%, or 500% more than the amount of biomass degrading enzyme produced without use of a composition comprising the caramelized sugar product or compared to the amount of biomass degrading enzyme produced by using an inducer biomass.

Use of a composition comprising a caramelized sugar product and an inducer biomass can result in an increase in the amount of protein, e.g., enzyme, e.g., amylase or biomass degrading enzyme produced. In an embodiment, the increase in the amount of biomass degrading enzyme produced by contacting a host cell or microorganism with a composition comprising a caramelized sugar product and an inducer biomass is at least 1 fold, 1.1 fold, 1.2 fold, 1.3 fold, 1.4 fold, 1.5 fold, 1.6 fold, 1.8 fold 1.9 fold, 2 fold, 2.1 fold, 2.2 fold, 2.3 fold, 2.4 fold, 2.5 fold, 2.6 fold, 2.7 fold, 2.8 fold, 2.9 fold, or 3 fold more, as compared to the amount of biomass degrading enzyme produced by using an inducer biomass alone or a caramelized sugar product alone. In an embodiment, the amount of biomass degrading enzyme produced by contacting a host cell or microorganism with a composition comprising a caramelized sugar product and an inducer biomass is at least 1%, 2%, 5%, 10%, 25%, 50%, 75%, 100%, 200%, 300%, 400%, or 500% more than the amount of biomass degrading enzyme produced by using an inducer biomass alone or a caramelized sugar product alone.

In some embodiments, the combination of a caramelized sugar product and an inducer biomass results in a synergistic increase in the amount of protein, e.g., enzyme, e.g., amylase or biomass degrading enzyme produced. In a synergistic effect, the observed effect from using a combination of two or more induction compositions is greater than the sum of the effect from using each individual induction composition separately. In an embodiment, a composition comprising a caramelized sugar product and an inducer biomass described herein can induce a synergistic effect in the biomass degrading enzyme production of a microorganism, and results in a yield of biomass degrading enzyme that is greater than the sum of the yields produced from inducing the microorganism with caramelized sugar product alone and the inducer biomass alone. In an embodiment, the amount of biomass degrading enzyme produced by contacting a host cell or microorganism with a composition comprising a caramelized sugar product and an inducer biomass is at least 1%, 2%, 5%, 10%, 25%, 50%, 75%, 100%, 200%, 300%, 400%, or 500% more than the sum of the amount of biomass degrading enzyme produced by using a caramelized sugar product alone and an inducer biomass alone.

The amount or titer of a protein, e.g., enzyme, e.g., amylase or biomass degrading enzyme produced by a microorganism can be determined using assays described in the examples described herein. For example, the amount of biomass degrading enzyme produced can be determined by using a Bradford assay and/or a nanodrop apparatus. For nanodrop protein quantification, the molar extinction coefficient can be estimated by inserting the amino acid sequence of the biomass degrading enzyme into the ExPASy ProtParam online tool. Activity assays known in the art can also be performed to determine the activity of the biomass degrading enzyme produced.

Inducing Production of Biomass Degrading Enzymes

The present disclosure provides compositions and methods for inducing the production of a protein, e.g., enzyme, e.g., amylase or biomass degrading enzyme. In embodiments, a composition comprising a caramelized sugar product described herein can be introduced to a microorganism or host cell under sufficient conditions for production of the biomass degrading enzyme. As used herein, producing or production of a biomass degrading enzyme by a microorganism includes the expression, translation, and/or secretion of the biomass degrading enzyme.

Microorganisms and Host Cells

The microorganism, or host cell, suitable for use in the present disclosure is capable of producing a protein, e.g., an enzyme, e.g., an amylase or a biomass degrading enzyme described herein. In an embodiment, the microorganism naturally produces a biomass degrading enzyme, e.g., expresses an endogenous biomass degrading enzyme. In an embodiment, the microorganism is genetically modified to produce a biomass degrading enzyme, e.g., to express a heterologous biomass degrading enzyme. In such embodiments, a nucleic acid encoding a heterologous biomass degrading enzyme is introduced to the microorganism using standard methods known in the art, e.g., by electroporation, transfection, or transduction. The heterologous biomass degrading enzyme may be a biomass degrading enzyme that is naturally produced in a different microorganism, or may be a modified biomass degrading enzyme comprising a different amino acid sequence or different function and/or activity, e.g., increased or decreased activity, from that of the corresponding naturally occurring biomass degrading enzyme.

The microorganism can be a fungus, a bacterium, a protozoan, a yeast, a synthetic organism or a semi-synthetic organism that produces one or more proteins, e.g., one or more enzymes, such as one or more amylases or biomass degrading enzymes. In an embodiment, the microorganism is from a species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*. In an embodiment, the microorganism is selected from *Aspergillus, Humicola insolens (Scytalidium thermophilum), Coprinus cinereus, Fusarium oxysporum, Myceliophthora thermophila, Meripilus giganteus, Thielavia ter-*

*restris, Acremonium persicinum, Acremonium acremonium, Acremonium brachypenium, Acremonium dichromosporum, Acremonium obclavatum, Acremonium pinkertoniae, Acremonium roseogriseum, Acremonium incoloratum, Acremonium furatum, Chrysosporium lucknowense, Trichoderma viride, Trichoderma reesei,* or *Trichoderma koningii.*

In embodiments, the microorganism is a fungus, e.g., a filamentous fungus. In an embodiment, the microorganism is *Trichoderma reesei* or any industrial strain or variant thereof. For example, the microorganism can be *T. reesei* QM6a, *T. reesei* RL-P37, *T. reesei* MCG-80, *T. reesei* RUTC30, *T. reesei* RUT-NG14, *T. reesei* PC3-7, or *T. reesei* QM9414.

Biomass Degrading Enzymes

Provided herein are compositions and methods for inducing production of a protein, e.g., an enzyme, e.g., an amylase or biomass degrading enzyme in a microorganism. The biomass degrading enzyme can be naturally expressed by the microorganism. The biomass degrading enzyme can be a cellulase (e.g., a cellobiase, a cellobiohydrolase, or an endoglucanase); a hemicellulase (e.g., a xylanase), or a ligninase, or any combination thereof.

In an embodiment, the biomass degrading enzyme is a cellulase. Cellulase collectively refers to enzymes that catalyze cellulolysis, or the decomposition of cellulose and related polysaccharides into monosaccharides, e.g., glucose or beta-glucose, or shorter polysaccharides and oligosaccharides. Cellulases are commonly produced by fungi, bacteria, and other protozoans. Examples of cellulases include cellobiases, cellobiohydrolases (exoglucanases), and endoglucanases.

In an embodiment, the biomass degrading enzyme is a cellobiase. A cellobiase is an enzyme that hydrolyzes beta-1,4 bonds in its substrate, e.g., cellobiose, to release two glucose molecules. Cellobiose is a water soluble 1,4-linked dimer of glucose. In an embodiment, the biomass degrading enzyme is Cel3a. Cel3a (also known as BglI) is a cellobiase that was identified in *Trichoderma reesei.*

In an embodiment, the biomass degrading enzyme is a cellobiohydrolase, also known as exoglucanase or avicelase. A cellobiohydrolase catalyzes the hydrolysis of 1-4-beta-D-glucosidic linkages in oligosaccharides containing that linkage, e.g., cellulose and cellotetraose, thereby releasing cellobiose from the non-reducing ends of the chains. Examples of cellobiohydrolases include cellobiohydrolase I (CBHI) and cellobiohydrolase II (CBHII) from *Trichoderma reesei.*

In an embodiment, the biomass degrading enzyme is an endoglucanase. An endoglucanase is an enzyme that catalyzes the hydrolysis of cellulose. Specifically, the endoglucanases cleave the internal bonds of the cellulose chain. Endoglucanases are produced by fungi, bacteria, and protozoans. Endoglucanases are also known as beta-1-4 endoglucanase, 4-beta-D-glucan cellobiohydrolase, exo-cellobiohydrolase, beta-1,4-glucan cellobiohydrolase, beta-1,4-glucan cellobiosylhydrolase, 1,4-beta-glucan cellobiosidase, C1 cellulase, cellobiohydrolase I, cellobiohydrolase, exo-beta-1,4-glucan cellobiohydrolase, 1,4-beta-D-glucan cellobiohydrolase, or cellobiosidase. Examples of endoglucanases include Cel5A, Cel5B, Cel7B, Cel12A, Cel45A, Cel61A, Cel61B, and Cel74A from *Trichoderma reesei.*

In an embodiment, the biomass degrading enzyme is a hemicellulase. A hemicellulase collectively refers to enzymes that hydrolyze hemicelluloses, e.g., various components of cell walls in plants with the exception of cellulose, e.g., xylans, glucans, galactans, mannans, and pentosans. Hemicellulases include xylanases and galactanases.

In an embodiment, the biomass degrading enzyme is a xylanase. Xylanases are also known as endo-(1-4)-beta-xylan 4-xylanohydrolase, endo-1,4-xylanase, endo-1,4-beta-xylanase, beta-1,4-xylanase, endo-1,4-beta-D-xylanase, 1,4-beta-xylan xylanohydrolase, beta-xylanase, beta-1,4-xylan xylanohydrolase, beta-D-xylanase. A xylanase breaks down a component of plant cell walls called hemicellulose, e.g., degrades polysaccharides, such as xylan, e.g., beta-1,4-xylan, glucuronoxylan, arabinoxylan, glucomannan, and xyloglucan, to release xylose. Examples of xylanases include Xyn1, Xyn2, and Xyn3 from *Trichoderma reesei*; and TERTU_1599, TERTU_3603, TERTU_2546, and TERTU_4506 from *Terendinibacter turnerae* T7901.

In an embodiment, the biomass degrading enzyme is a ligninase. A ligninase is an enzyme that breaks down lignin, which is a complex polymer of aromatic alcohols known as monolignols and plays an integral part of the secondary cell walls of plants and some algae. Ligninases include lignin peroxidases, 1,2-bis(3,4-dimethoxyphenyl)propane-1,3-diol:hydrogen-peroxide oxidoreductase, diarylpropane oxygenase, ligninase I, diarylpropane peroxidase, LiP, hydrogen-peroxide oxidoreductase (C—C-bond-cleaving), and some laccases. Examples of ligninases include CIP2 from *Trichoderma reesei*; LPOA, GLG2, GLG4, LIPA, GLG5, GLG3, GLG6, and LIPB from *Phanerochaete chrysosporium*; ligninase-3 from *Phelbia radiate*; Ligninase A and B from *Coriolus versicolor*; and LPG I and LPGIV *Coriolus versicolor.*

In embodiments, the methods described herein are used to induce production of one or more cellulases or hemicellulases, e.g., one or more of a cellobiase, a cellobiohydrolase, an endoglucanase, a xylanase, and/or a ligninase. In an embodiment, the methods described herein are used to induce production of a mixture of biomass degrading enzymes comprising any combination of one or more of a cellobiase, a cellobiohydrolase, an endoglucanase, a xylanase, and/or a ligninase. In embodiments, the mixture of biomass degrading enzymes comprises at least 2, at least 3, at least 4, at least 5, at least 6, at least 7, at least 8, at least 9, at least 10, at least 11, at least 12, at least 15, or at least 20 biomass degrading enzymes, e.g., biomass degrading enzymes described herein.

Exemplary biomass degrading enzymes are listed in Table 1.

TABLE 1

Examples of Biomass Degrading Enzymes

| Protein | MW, kDa | no AA's | th. pI | no. Cysteines | Organism |
|---|---|---|---|---|---|
| B2AF03 | 87.1 | 800 | 5.94 | 10 | *Podospora anserina* |
| CIP1 | 32.9 | 316 | 4.93 | 8 | *Trichoderma reesei* |
| CIP2 | 48.2 | 460 | 7.0 | 12 | *Trichoderma reesei* |
| Cel1a | 52.2 | 466 | 5.3 | 5 | *Trichoderma reesei* |
| Cel3a | 78.4 | 744 | 6.3 | 6 | *Trichoderma reesei* |
| Cel5a | 44.1 | 418 | 4.9 | 12 | *Trichoderma reesei* |
| Cel6a | 49.6 | 471 | 5.1 | 12 | *Trichoderma reesei* |
| Cel7a | 54.1 | 514 | 4.6 | 24 | *Trichoderma reesei* |
| Cel7b | 48.2 | 459 | 4.7 | 22 | *Trichoderma reesei* |
| Cel12a | 25.1 | 234 | 6.6 | 2 | *Trichoderma reesei* |
| Cel45a | 24.4 | 242 | 4.2 | 16 | *Trichoderma reesei* |
| Cel74a | 87.1 | 838 | 5.4 | 4 | *Trichoderma reesei* |
| paMan5a | 41.1 | 373 | 7.0 | 6 | *Podospora anserina* |
| paMan26a | 51.7 | 469 | 4.7 | 1 | *Podospora anserina* |
| Swollenin | 51.5 | 493 | 4.8 | 28 | *Trichoderma reesei* |

In an embodiment, the biomass degrading enzyme produced by the methods described herein is Cel3a, e.g., a Cel3a from *T. reesei*. In an embodiment, the mixture of biomass degrading enzymes comprises at least 2, 3, 4, 5, 6, 7, 8, 9, 10, 11, 12, 13, 14, or 15 of the biomass degrading enzymes listed in Table 1.

The amino acid sequences for the biomass degrading enzymes listed in Table 1 are provided below.

B2AF03 (Podospora anserina)
(SEQ ID NO: 1)
MKSSVFWGASLTSAVVRAIDLPFQFYPNCVDDLLSTNQVCNTTLSPPERA
AALVAALTPEEKLQNIVSKSLGAPRIGLPAYNWWSEALHGVAYAPGTQFW
QGDGPFNSSTSFPMPLLMAATFDDELLEKIAEVIGIEGRAFGNAGFSGLD
YWTPNVNPFKDPRWGRGSETPGEDVLLVKRYAAAMIKGLEGPVPEKERRV
VATCKHYAANDFEDWNGATRHNFNAKISLQDMAEYYFMPFQQCVRDSRVG
SIMCAYNAVNGVPSCASPYLLQTILREHWNWTEHNNYITSDCEAVLDVSL
NHKYAATNAEGTAISFEAGMDTSCEYEGSSDIPGAWSQGLLKESTVDRAL
LRLYEGIVRAGYFDGKQSLYSSLGWADVNKPSAQKLSLQAAVDGTVLLKN
DGTLPLSDLLDKSRPKKVAMIGFWSDAKDKLRGGYSGTAAYLHTPAYAAS
QLGIPFSTASGPILHSDLASNQSWTDNAMAAAKDADYILYFGGIDTSAAG
ETKDRYDLDWPGAQLSLINLLTTLSKPLIVLQMGDQLDNTPLLSNPKINA
ILWANWPGQDGGTAVMELVTGLKSPAGRLPVTQYPSNFTELVPMTDMALR
PSAGNSQLGRTYRWYKTPVQAFGFGLHYTTFSPKFGKKFPAVIDVDEVLE
GCDDKYLDTCPLPDLPVVVENRGNRTSDYVALAFVSAPGVGPGPWPIKTL
GAFTRLRGVKGGEKREGGLKWNLGNLARHDEEGNTVVYPGKYEVSLDEPP
KARLRFEIVRGGKGKGKVKGKGKAAQKGGVVLDRWPKPPKGQEPPAIERV CIP1 (Trichoderma reesei)
(SEQ ID NO: 2)
MVRRTALLALGALSTLSMAQISDDFESGWDQTKWPISAPDCNQGGTVSLD
TTVAHSGSNSMKVVGGPNGYCGHIFFGTTQVPTGDVYVRAWIRLQTALGS
NHVTFIIMPDTAQGGKHLRIGGQSQVLDYNRESDDATLPDLSPNGIASTV
TLPTGAFQCFEYHLGTDGTIETWLNGSLIPGMTVGPGVDNPNDAGWTRAS
YIPEITGVNFGWEAYSGDVNTVWFDDISIASTRVGCGPGSPGGPGSSTTG
RSSTSGPTSTSRPSTTIPPPTSRTTTATGPTQTHYGQCGGIGYSGPTVCA
SGTTCQVLNPYYSQCL CIP2 (Trichoderma reesei)
(SEQ ID NO: 3)
MASRFFALLLLAIPIQAQSPVWGQCGGIGWSGPTTCVGGATCVSYNPYYS
QCIPSTQASSSIASTTLVTSFTTTTATRTSASTPPASSTGAGGATCSALP
GSITLRSNAKLNDLFTMFNGDKVTTKDKFSCRQAEMSELIQRYELGTLPG
RPSTLTASFSGNTLTINCGEAGKSISFTVTITYPSSGTAPYPAIIGYGGG
SLPAPAGVAMINFNNDNIAAQVNTGSRGQGKFYDLYGSSHSAGAMTAWAW
GVSRVIDALELVPGARIDTTKIGVTGCSRNGKGAMVAGAFEKRIVLTLPQ
ESGAGGSACWRISDYLKSQGANIQTASEIIGEDPWFSTTFNSYVNQVPVL
PFDHHSLAALIAPRGLFVIDNNIDWLGPQSCFGCMTAAHMAWQALGVSDH
MGYSQIGAHAHCAFPSNQQSQLTAFVQKFLLGQSTNTAIFQSDFSANQSQ
WIDWTTPTLS Cel1a (Trichoderma reesei)
(SEQ ID NO: 4)
MLPKDFQWGFATAAYQIEGAVDQDGRGPSIWDTFCAQPGKIADGSSGVTA
CDSYNRTAEDIALLKSLGAKSYRFSISWSRIIPEGGRGDAVNQAGIDHYV
KFVDDLLDAGITPFITLFHWDLPEGLHQRYGGLLNRTEFPLDFENYARVM
FRALPKVRNWITFNEPLCSAIPGYGSGTFAPGRQSTSEPWTVGHNILVAH
GRAVKAYRDDFKPASGDGQIGIVLNGDFTYPWDAADPADKEAAERRLEFF
TAWFADPIYLGDYPASMRKQLGDRLPTFTPEERALVHGSNDFYGMNHYTS
NYIRHRSSPASADDTVGNVDVLFTNKQGNCIGPETQSPWLRPCAAGFRDF
LVWISKRYGYPPIYVTENGTSIKGESDLPKEKILEDDFRVKYYNEYIRAM
VTAVELDGVNVKGYFAWSLMDNFEWADGYVTRFGVTYVDYENGQKRFPKK
SAKSLKPLFDELIAAA Cel3a (Trichoderma reesei)
(SEQ ID NO: 5)
MRYRTAAALALATGPFARADSHSTSGASAEAVVPPAGTPWGTAYDKAKAA
LAKLNLQDKVGIVSGVGWNGGPCVGNTSPASKISYPSLCLQDGPLGVRYS
TGSTAFTPGVQAASTWDVNLIRERGQFIGEEVKASGIHVILGPVAGPLGK
TPQGGRNWEGFGVDPYLTGIAMGQTINGIQSVGVQATAKHYILNEQELNR
ETISSNPDDRTLHELYTWPFADAVQANVASVMCSYNKVNTTWACEDQYTL
QTVLKDQLGFPGYVMTDWNAQHTTVQSANSGLDMSMPGTDFNGNNRLWGP
ALTNAVNSNQVPTSRVDDMVTRILAAWYLTGQDQAGYPSFNISRNVQGNH
KTNVRAIARDGIVLLKNDANILPLKKPASIAVVGSAAIIGNHARNSPSCN
DKGCDDGALGMGWGSGAVNYPYFVAPYDAINTRASSQGTQVTLSNTDNTS
SGASAARGKDVAIVFITADSGEGYITVEGNAGDRNNLDPWHNGNALVQAV
AGANSNVIVVVHSVGAIILEQILALPQVKAVVWAGLPSQESGNALVDVLW
GDVSPSGKLVYTIAKSPNDYNTRIVSGGSDSFSEGLFIDYKHFDDANITP
RYEFGYGLSYTKFNYSRLSVLSTAKSGPATGAVVPGGPSDLFQNVATVTV
DIANSGQVTGAEVAQLYITYPSSAPRTPPKQLRGFAKLNLTPGQSGTATF
NIRRRDLSYWDTASQKWVVPSGSFGISVGASSRDIRLTSTLSVA Cel5a (Trichoderma reesei)
(SEQ ID NO: 6)
MNKSVAPLLLAASILYGGAAAQQTVWGQCGGIGWSGPTNCAPGSACSTLN
PYYAQCIPGATTITTSTRPPSGPTTTTRATSTSSSTPPTSSGVRFAGVNI
AGFDFGCTTDGTCVTSKVYPPLKNFTGSNNYPDGIGQMQHFVNDDGMTIF
RLPVGWQYLVNNNLGGNLDSTSISKYDQLVQGCLSLGAYCIVDIHNYARW
NGGIIGQGGPTNAQFTSLWSQLASKYASQSRVWFGIMNEPHDVNINTWAA
TVQEVVTAIRNAGATSQFISLPGNDWQSAGAFISDGSAAALSQVTNPDGS
TTNLIFDVHKYLDSDNSGTHAECTTNNIDGAFSPLATWLRQNNRQAILTE
TGGGNVQSCIQDMCQQIQYLNQNSDVYLGYVGWGAGSFDSTYVLTETPTG
SGNSWTDTSLVSSCLARK Cel6a (Trichoderma reesei)
(SEQ ID NO: 7)
MIVGILTTLATLATLAASVPLEERQACSSVWGQCGGQNWSGPTCCASGST
CVYSNDYYSQCLPGAASSSSSTRAASTTSRVSPTTSRSSSATPPPGSTTT
RVPPVGSGTATYSGNPFVGVTPWANAYYASEVSSLAIPSLTGAMATAAAA -continued VAKVPSFMWLDTLDKTPLMEQTLADIRTANKNGGNYAGQFVVYDLPDRDC
AALASNGEYSIADGGVAKYKNYIDTIRQIVVEYSDIRTLLVIEPDSLANL
VTNLGTPKCANAQSAYLECINYAVTQLNLPNVAMYLDAGHAGWLGWPANQ
DPAAQLFANVYKNASSPRALRGLATNVANYNGWNITSPPSYTQGNAVYNE
KLYIHAIGPLLANHGWSNAFFITDQGRSGKQPTGQQQWGDWCNVIGTGFG
IRPSANTGDSLLDSFVWVKPGGECDGTSDSSAPRFDSHCALPDALQPAPQ
AGAWFQAYFVQLLTNANPSFL Cel7a (Trichoderma reesei)
(SEQ ID NO: 8)
MYRKLAVISAFLATARAQSACTLQSETHPPLTWQKCSSGGTCTQQTGSVV
IDANWRWTHATNSSTNCYDGNTWSSTLCPDNETCAKNCCLDGAAYASTYG
VTTSGNSLSIGFVTQSAQKNVGARLYLMASDTTYQEFTLLGNEFSFDVDV
SQLPCGLNGALYFVSMDADGGVSKYPTNTAGAKYGTGYCDSQCPRDLKFI
NGQANVEGWEPSSNNANTGIGGHGSCCSEMDIWEANSISEALTPHPCTTV
GQEICEGDGCGGTYSDNRYGGTCDPDGCDWNPYRLGNTSFYGPGSSFTLD
TTKKLTVVTQFETSGAINRYYVQNGVTFQQPNAELGSYSGNELNDDYCTA
EEAEFGGSSFSDKGGLTQFKKATSGGMVLVMSLWDDYYANMLWLDSTYPT
NETSSTPGAVRGSCSTSSGVPAQVESQSPNAKVTFSNIKFGPIGSTGNPS
GGNPPGGNPPGTTTTRRPATTTGSSPGPTQSHYGQCGGIGYSGPTVCASG
TTCQVLNPYYSQCL Cel7b (Trichoderma reesei)
(SEQ ID NO: 9)
MAPSVTLPLTTAILAIARLVAAQQPGTSTPEVHPKLTTYKCTKSGGCVAQ
DTSVVLDWNYRWMHDANYNSCTVNGGVNTTLCPDEATCGKNCFIEGVDYA
ASGVTTSGSSLTMNQYMPSSSGGYSSVSPRLYLLDSDGEYVMLKLNGQEL
SFDVDLSALPCGENGSLYLSQMDENGGANQYNTAGANYGSGYCDAQCPVQ
TWRNGTLNTSHQGFCCNEMDILEGNSRANALTPHSCTATACDSAGCGFNP
YGSGYKSYYGPGDTVDTSKTFTIITQFNTDNGSPSGNLVSITRKYQQNGV
DIPSAQPGGDTISSCPSASAYGGLATMGKALSSGMVLVFSIWNDNSQYMN
WLDSGNAGPCSSTEGNPSNILANNPNTHVVFSNIRWGDIGSTTNSTAPPP
PPASSTTFSTTRRSSTTSSSPSCTQTHWGQCGGIGYSGCKTCTSGTTCQY
SNDYYSQCL Cel12a (Trichoderma reesei)
(SEQ ID NO: 10)
MKFLQVLPALIPAALAQTSCDQWATFTGNGYTVSNNLWGASAGSGFGCVT
AVSLSGGASWHADWQWSGGQNNVKSYQNSQIAIPQKRTVNSISSMPTTAS
WSYSGSNIRANVAYDLFTAANPNHVTYSGDYELMIWLGKYGDIGPIGSSQ
GTVNVGGQSWTLYYGYNGAMQVYSFVAQTNTTNYSGDVKNFFNYLRDNKG
YNAAGQYVLSYQFGTEPFTGSGTLNVASWTASIN Cel45a (Trichoderma reesei)
(SEQ ID NO: 11)
MKATLVLGSLIVGAVSAYKATTTRYYDGQEGACGCGSSSGAFPWQLGIGN
GVYTAAGSQALFDTAGASWCGAGCGKCYQLTSGQAPCSSCGTGGAAGQS
IIVMVTNLCPNNGNAQWCPVVGGTNQYGYSYHFDIMAQNEIFGDNVVDF EPIACPGQAASDWGTCLCVGQQETDPTPVLGNDTGSTPPGSSPPATSSSP
PSGGGQQTLYGQCGGAGWTGPTTCQAPGTCKVQNQWYSQCLP Cel74a (Trichoderma reesei)
(SEQ ID NO: 12)
MKVSRVLALVLGAVIPAHAAFSWKNVKLGGGGGFVPGIIFHPKTKGVAYA
RTDIGGLYRLNADDSWTAVTDGIADNAGWHNWGIDAVALDPQDDQKVYAA
VGMYTNSWDPSNGAIIRSSDRGATWSFTNLPFKVGGNMPGRGAGERLAVD
PANSNIIYFGARSGNGLWKSTDGGVTFSKVSSFTATGTYIPDPSDSNGYN
SDKQGLMWVTFDSTSSTTGGATSRIFVGTADNITASVYVSTNAGSTWSAV
PGQPGKYFPHKAKLQPAEKALYLTYSDGTGPYDGTLGSVWRYDIAGGTWK
DITPVSGSDLYFGFGGLGLDLQKPGTLVVASLNSWWPDAQLFRSTDSGTT
WSPIWAWASYPTETYYYSISTPKAPWIKNNFIDVTSESPSDGLIKRLGWM
IESLEIDPTDSNHWLYGTGMTIFGGHDLTNWDTRHNVSIQSLADGIEEFS
VQDLASAPGGSELLAAVGDDNGFTFASRNDLGTSPQTVWATPTWATSTSV
DYAGNSVKSVVRVGNTAGTQQVAISSDGGATWSIDYAADTSMNGGTVAYS
ADGDTILWSTASSGVQRSQFQGSFASVSSLPAGAVIASDKKTNSVFYAGS
GSTFYVSKDTGSSFTRGPKLGSAGTIRDIAAHPTTAGTLYVSTDVGIFRS
TDSGTTFGQVSTALTNTYQIALGVGSGSNWNLYAFGTGPSGARLYASGDS
GASWTDIQGSQGFGSIDSTKVAGSGSTAGQVYVGTNGRGVFYAQGTVGGG
TGGTSSSTKQSSSSTSSASSSTTLRSSVVSTTRASTVTSSRTSSAAGPTG
SGVAGHYAQCGGIGWTGPTQCVAPYVCQKQNDYYYQCV paMan5a (Podospora anserina)
(SEQ ID NO: 13)
MKGLFAFGLGLLSLVNALPQAQGGGAAASAKVSGTRFVIDGKTGYFAGTN
SYWIGFLTNNRDVDTTLDHIASSGLKILRVWGFNDVNNQPSGNTVWFQRL
ASSGSQINTGPNGLQRLDYLVRSAETRGIKLIIALVNYWDDFGGMKAYVN
AFGGTKESWYTNARAQEQYKRYIQAVVSRYVNSPAIFAWELANEPRCKGC
NTNVIFNWATQISDYIRSLDKDHLITLGDEGFGLPGQTTYPYQYGEGTDF
VKNLQIKNLDFGTFHMYPGHWGVPTSFGPGWIKDHAAACRAAGKPCLLEE
YGYESDRCNVQKGWQQASRELSRDGMSGDLFWQWGDQLSTGQTHNDGFTI
YYGSSLATCLVTDHVRAINALPA paMan26a (Podospora anserina)
(SEQ ID NO: 14)
MVKLLDIGLFALALASSAVAKPCKPRDGPVTYEAEDAILTGTTVDTAQVG
YTGRGYVTGFDEGSDKITFQISSATTKLYDLSIRYAAIYGDKRTNVVLNN
GAVSEVFFPAGDSFTSVAAGQVLLNAGQNTIDIVNNWGWYLIDSITLTPS
APRPPHDINPNLNNPNADTNAKKLYSYLRSVYGNKIISGQQELHHAEWIR
QQTGKTPALVAVDLMDYSPSRVERGTTSHAVEDAIAHHNAGGIVSVLWHW
NAPVGLYDTEENKWWSGFYTRATDFDIAATLANPQGANYTLLIRDIDAIA
VQLKRLEAAGVPVLWRPLHEAEGGWFWWGAKGPEPAKQLWDILYERLTVH
HGLDNLIWVWNSILEDWYPGDDTVDILSADVYAQGNGPMSTQYNELIALG
RDKKMIAAAEVGAAPLPGLLQAYQANWLWFAVWGDDFINNPSWNTVAVLN
EIYNSDYVLTLDEIQGWRS -continued Swollenin (*Trichoderma reesei*)
(SEQ ID NO: 15)
MAGKLILVALASLVSLSIQQNCAALFGQCGGIGWSGTTCCVAGAQCSFVN

DWYSQCLASTGGNPPNGTTSSSLVSRTSSASSSVGSSSPGGNSPTGSAST

YTTTDTATVAPHSQSPYPSIAASSCGSWTLVDNVCCPSYCANDDTSESCS

GCGTCTTPPSADCKSGTMYPEVHHVSSNESWHYSRSTHFGLTSGGACGFG

LYGLCTKGSVTASWTDPMLGATCDAFCTAYPLLCKDPTGTTLRGNFAAPN

GDYYTQFWSSLPGALDNYLSCGECIELIQTKPDGTDYAVGEAGYTDPITL

EIVDSCPCSANSKWCCGPGADHCGEIDFKYGCPLPADSIHLDLSDIAMGR

LQGNGSLTNGVIPTRYRRVQCPKVGNAYIWLRNGGGPYYFALTAVNTNGP

GSVTKIEIKGADTDNWVALVHDPNYTSSRPQERYGSWVIPQGSGPFNLPV

GIRLTSPTGEQIVNEQAIKTFTPPATGDPNFYYIDIGVQFSQN

In embodiments, the biomass degrading enzyme comprises an amino acid sequence with at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to a biomass degrading enzyme described herein, e.g., listed in Table 1, or a functional fragment thereof, e.g., at least 80%, at least 85%, at least 90%, at least 91%, at least 92%, at least 93%, at least 94%, at least 95%, at least 96%, at least 97%, at least 98%, or at least 99% identity to a biomass degrading enzyme described herein, e.g., listed in Table 1, or a functional fragment thereof.

Percent identity in the context of two or more amino acid or nucleic acid sequences, refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides, 100 nucleotides, 150 nucleotides, in length. More preferably, the identity exists over a region that is at least about 200 or more amino acids, or at least about 500 or 1000 or more nucleotides, in length.

For sequence comparison, one sequence typically acts as a reference sequence, to which one or more test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

Functional variants may comprise one or more mutations, such that the variant retains some level of activity, e.g., biomass degrading activity, of an enzyme, e.g., a biomass degrading enzyme described herein produced by the microorganism from which the enzyme originates from. In an embodiment, the functional variant has at least 10%, at least 20%, at least 30%, at least 40%, at least 50%, at least 60%, at least 70%, at least 75%, at least 80%, at least 85%, at least 90%, at least 95%, or at least 99% (e.g., at least 80%, at least 85%, at least 90%, at least 95%, or at least 99%) of the biomass degrading activity as the corresponding naturally occurring biomass degrading enzyme. In embodiments, the functional variant has at least 200%, at least 300%, at least 400%, at least 500%, at least 1000% or more of the biomass degrading activity as the corresponding naturally occurring biomass degrading enzyme. Biomass degrading activity can be tested using the functional assays known in the art. For example, if the biomass degrading enzyme is a cellulase, then functional assays that measure cellulase activity can be performed.

The mutations present in a functional variant include amino acid substitutions, additions, and deletions. Mutations can be introduced by standard techniques known in the art, such as site-directed mutagenesis and PCR-mediated mutagenesis. Mutagenesis can also be achieved through using CRISPR (Clustered regularly-interspaced short palindromic repeats)/Cas systems. The CRISPR/Cas system is naturally found in bacteria and archaea, and has been modified for use in gene editing (silencing, enhancing or mutating specific genes) in eukaryotes such as mice or primates. Wiedenheft et al. (2012) *Nature* 482: 331-8. This is accomplished by introducing into the cell a plasmid containing a specifically designed CRISPR and one or more appropriate Cas.

The mutation may be a conservative amino acid substitution, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the biomass degrading enzyme can be replaced with other amino acids from the same side chain family, and the resultant biomass degrading activity comparable (e.g., at least 80%, 85%, 90%, 95%, or 99% of the biomass degrading activity) to that of the wild-type biomass degrading enzyme. Alternatively, the mutation may be an amino acid substitution in which an amino acid residue is replaced with an amino acid residue having a different side chain.

Such mutations may alter or affect various enzymatic characteristics of the biomass degrading enzyme, e.g., cellobiase, ligninase, endoglucanase, or cellobiohydrolase. For example, such mutations may alter or affect the activity, e.g., the biomass degrading activity, thermostability, optimal pH for reaction, enzyme kinetics, or substrate recognition of the enzyme, e.g., the biomass degrading enzyme. In some embodiments, a mutation increases the biomass degrading activity of the variant in comparison to the biomass degrading enzyme, e.g., a cellulase produced by *T. reesei*. In some embodiments, a mutation increases or decreases the thermostability of the variant in comparison to a wild-type biomass degrading enzyme, e.g., a cellulase produced by *T. reesei*. In an embodiment, a mutation changes the pH range at which the variant optimally performs the biomass degrading reaction in comparison to wild-type biomass degrading enzyme, e.g., a cellulase produced by *T. reesei*. In an embodiment, a mutation increases or decreases the kinetics of the biomass degrading reaction (e.g., $k_{cat}$, $K_M$, $k_{cat}/K_M$, or $K_D$) in comparison to wild-type biomass degrading enzyme, e.g., a cellulase produced by *T. reesei*. In an embodiment, a mutation increases or decreases the ability of the cellobiase to recognize or bind to the substrate in comparison to wild-type biomass degrading enzyme, e.g., a cellulase produced by *T. reesei*.

Cell Culture and Induction

The microorganism that can produce a protein, e.g., enzyme, e.g., amylase or biomass degrading enzyme can be in a cell culture. A cell culture comprises one or more cells in a cell culture medium. The cell culture medium can be an aqueous cell culture medium comprising components that support cell maintenance, cell viability, cell growth, and/or cell proliferation. Cell culture media can typically comprises physiological salts, e.g., ammonium salt, phosphate salt, potassium salt, magnesium salt, calcium salt, iron salt, manganese salt, zinc salt, or cobalt salt; amino acids; water, and optionally, a carbon source. In an embodiment, a cell culture media suitable for growing a microorganism described herein comprises an ammonium salt, e.g., ammonium sulfate and/or ammonium hydroxide; a potassium salt, e.g., potassium hydroxide; a calcium salt, e.g., calcium chloride; a magnesium salt, e.g., magnesium sulfate; a manganese salt, e.g., manganese sulfate; an iron salt, e.g., iron sulfate; a zinc salt, e.g., zinc sulfate, a cobalt salt, e.g., cobalt chloride, phthalic acid; lactose; antibiotics, e.g., ACETOBAN®; and a carbon source, e.g., glucose. An exemplary growth media is summarized in Table 2 and 3.

The microorganism or cell culture is contacted with, e.g., fed, a carbon source, such as a sugar, to support the growth or proliferation of the microorganism. In an embodiment, the microorganism or cell culture is contacted with, e.g., fed, glucose.

As the microorganism proliferates in culture, the cell culture can be transferred from one container, e.g., a cell culture container, to a larger container to allow and encourage the microorganism to continue to proliferate. For example, the microorganism is contacted with sugar in a first container under suitable conditions, as described herein, such that the microorganism proliferates. The proliferation can be monitored, and once a desired level of growth, e.g., a specific growth phase, or a desired level of proliferation, e.g., as measured by turbidity of the culture or by cell number, the microorganism can be transferred to a second container, where the second container is larger, e.g., by volume, than the first container. Transferring the microorganism to the larger second container allows and encourages the microorganism to continue to proliferate. In embodiments, the microorganism is transferred once, e.g., from a first container to a larger second container. In embodiments, the microorganism is transferred more than once, e.g., two, three, four, five, six, seven, eight, nine, or ten times, wherein for each transfer, the microorganism is transferred into a container that is larger than the container from which the microorganism was transferred from.

Containers suitable for transferring and culturing the microorganisms described herein include any cell culture container known in the art. Examples of suitable containers include, but are not limited to, a cell culture flask, a roller bottle, a bioreactor, or a tank.

Other cell culture conditions appropriate for maintaining cell viability or promoting cell proliferation are known in the art. Cell culture conditions for consideration include pH, temperature, oxygen levels, and movement. The pH of the cell culture, e.g., the media, is generally at physiological pH, e.g., between pH 4-8, or between pH 5-7, e.g., at pH 5, pH 6, or pH 7. The temperature for growth of a microorganism producing a biomass degrading enzyme is generally between 20 and 40° C., e.g., 30° C. In some embodiments, a particular strain of the microorganism may show enhanced proliferation of enzyme production at an elevated temperature, e.g., 32 or 37° C., or at a lower temperature, e.g., 27° C. Optimal oxygen levels for growth of a microorganism producing a biomass degrading enzyme is generally between 15 and 30%, e.g., 20%. The cell culture may be stationary or may use movement to promote maintenance or proliferation. For example, the cell culture may be rolled, shaken, or agitated to enhance cell proliferation. The cell culture conditions disclosed herein are merely exemplary, and should not be construed as limiting. Varying cell culture conditions from those explicitly listed herein may be envisioned or experimentally determined, and may depend on the species or strain of microorganism used. Cell culture conditions sufficient for proliferation of the microorganism that can produce a biomass degrading enzyme result in an increase in the cell number of a culture of the microorganism. Cell culture conditions sufficient for the production of a biomass degrading enzyme results in one or more cells of the microorganism producing a biomass degrading enzyme.

Once the cell culture has achieved a desired level of growth, e.g., a specific growth phase or culture volume size, or when the cell culture, e.g., the aqueous portion, is substantially free from the carbon source, e.g., sugar, utilized to stimulate proliferation, the cell culture can be induced to produce a protein, e.g., an enzyme, e.g., an amylase or biomass degrading enzyme described herein. A composition described herein comprising a caramelized sugar product is added e.g., fed, to the microorganism or cell culture that is capable of producing a biomass degrading enzyme, thereby inducing the microorganism to produce the biomass degrading enzyme. In an embodiment, the composition comprising a caramelized sugar product is added to the culture directly. In an embodiment, the composition comprising a caramelized sugar product is added to an enzyme production culture media, comprising components that support and encourage the production of the protein, e.g., biomass degrading enzyme. The microorganism is then transferred or cultured in the enzyme production culture media. An enzyme production culture media can comprise physiological salts, e.g., ammonium salts, and a composition comprising a caramelized sugar product and/or an inducer biomass, and is adjusted to pH 4-7, e.g., pH 6. In an embodiment, an enzyme production culture media comprises ammonium sulfate, rice bran, and a composition comprising a caramelized sugar product and/or an inducer biomass, e.g., corncob or beeswing, and is adjusted to pH 6, e.g., with 6M ammonium hydroxide.

Production of a protein, e.g., an enzyme, e.g., an amylase or biomass degrading enzyme can be induced by contacting the microorganism with a combination of a caramelized sugar product and an inducer biomass described herein. The inducer biomass can be a starchy material comprising cellulose. The biomass may also comprise hemicellulose and/or lignin. The inducer biomass can comprise one or more of an agricultural product or waste, a paper product or waste, a forestry product, or a general waste, or any combination thereof. An agricultural product or waste comprises material that can be cultivated, harvested, or processed for use or consumption, e.g., by humans or animals, or any intermediate, byproduct, or waste that is generated from the cultivation, harvest, or processing methods. Agricultural products or waste include, but are not limited to, sugar cane, jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof. A paper product or waste comprises material that is used to make a paper product, any paper product, or any intermediate, byproduct or waste that is generated from making or breaking down the paper product. Paper products or waste include, but are not limited to, paper, pigmented papers, loaded papers, coated papers, corrugated paper, filled papers, magazines, printed matter, printer paper, polycoated paper, cardstock, cardboard, paperboard, or paper pulp, or a combination thereof. A forestry product or waste comprises material that is produced by cultivating, harvesting, or processing of wood, or any intermediate, byproduct, or waste that is generated from the cultivation, harvest, or processing of the wood. Forestry products or waste include, but are not limited to, aspen wood, wood from any genus or species of tree, particle board, wood chips, or sawdust, or a combination thereof. A general waste includes, but is not limited to, manure, sewage, or offal, or a combination thereof.

In an embodiment, a caramelized sugar product and an inducer biomass are added to the microorganism or cell culture simultaneously. The caramelized sugar product and the inducer biomass can be present in the same composition or can be in separate compositions. When the caramelized sugar product and inducer biomass are present in the same composition, the caramelized sugar product and inducer biomass can be components of an enzyme production culture media. In another embodiment, a caramelized sugar product and an inducer biomass are in separate compositions, and are added to the microorganism or cell culture sequentially. For example, a caramelized sugar product can be added to the microorganism or cell culture prior to or after an inducer biomass is added to the microorganism or cell culture. In such sequential induction processes, the duration between the addition of the caramelized sugar product and the addition of an inducer biomass can be hours, e.g., 1, 2, 3, 4, 5, 6, 12, 18, or more hours, or days, e.g., 1, 2, 3, 4, 5, 6, 7 or more days.

A caramelized sugar product can be introduced to the microorganism, e.g., by direct addition to the culture or by enzyme production culture media, twice a day, once a day, every other day, every three days or once a week. The caramelized sugar product can be added at a concentration range of 1-20 g/L, 1-15 g/L, 1-10 g/L, 1-5 g/L, 2-15 g/L, 2-10 g/L, 2-5 g/L, 5-20 g/L, 5-15 g/L, 5-10 g/L, 4-5 g/L, 10-20 g/L or 10-15 g/L of microorganism cell culture. The caramelized sugar product can be added at a concentration of 0.5 g/L, 1 g/L, 2 g/L, 3 g/L, 4 g/L, 5 g/L, 6 g/L, 7 g/L, 8 g/L, 9 g/L, 10 g/L, 15 g/L or 20 g/L or more, of microorganism cell culture. In an embodiment, the caramelized sugar product is added to the microorganism at 4 g/L once per day, or 5 g/L once per day.

An inducer biomass can be introduced to the microorganism, e.g., by direct addition to the culture or by enzyme production culture media, twice a day, once a day, every other day, every 3 days, or once a week. The inducer biomass can be added at a concentration range of 1-20 g/L, 1-15 g/L, 1-10 g/L, 1-5 g/L, 2-15 g/L, 2-10 g/L, 2-5 g/L, 5-20 g/L, 5-15 g/L, 5-10 g/L, 10-20 g/L, or 10-15 g/L of microorganism cell culture. The inducer biomass can be added at a concentration of 0.5 g/L, 1 g/L, 2 g/L, 3 g/L, 4 g/L, 5 g/L, 6 g/L, 7 g/L, 8 g/L, 9 g/L, 10 g/L, 15 g/L or 20 g/L or more, of microorganism cell culture. In an embodiment, the inducer biomass is added to the microorganism at 5 g/L, once per day.

In embodiments, the concentration of a caramelized sugar product or an inducer biomass used for inducing production of a protein, e.g., an enzyme, e.g., an amylase or biomass degrading enzyme is greater than or equal to 0.1% weight by volume (w/v), 0.5% w/v, 1% w/v, 2% w/v, or 5% w/v, and less than or equal to 25% w/v, 20% w/v, 15% w/v, and 10% w/v.

The microorganism can be induced to produce a protein, e.g., an enzyme, e.g., an amylase or biomass degrading enzyme for one or more days, e.g., 2, 3, 4, 5, 6, 7, 8, 9, 10, 11, 12, 13, 14, 15, 20, or 30 or more days. The duration of the induction can depend on the size, e.g., volume or cell number, of the microorganism culture, the microorganism used, or the amount of the protein, e.g., enzyme, e.g., amylase or biomass degrading enzyme needed. In an embodiment, the microorganism is induced to produce a biomass degrading enzyme for 11 or 12 days.

Production of the protein, e.g., enzyme, e.g., amylase or biomass degrading enzyme can be measured from the cell culture by measuring the level of proteins, e.g. biomass degrading enzymes, present in the cell culture that were produced by the cells. For example, the aqueous portion of the culture can be isolated, e.g., by centrifuging the cell culture or an aliquot or sample of the cell culture. A protein assay known in the art, such as the Bradford assay or nanodrop protein quantification, can be used to determine the level or titer of protein, e.g., g/L, in the aqueous portion of the culture. The protein titer indicates the amount of biomass degrading enzyme produced by the microorganism or cell culture. A control sample can be used to normalize for the amount of proteins present in a cell culture that has not been induced to produce a biomass degrading enzyme.

The proteins, e.g., enzymes, e.g., amylases or biomass degrading enzymes produced by the microorganism as described herein can be used in biological or industrial processes, such as processing biomass materials described herein into products, e.g., sugar products or biofuels. Methods for process biomass materials into products, e.g., degrading or converting biomass materials into sugars or biofuels, are described further herein. The microorganism, or culture thereof, that has been induced to produce a protein, e.g., a biomass degrading enzyme, as described herein, can be added directly to the biomass to be processed. Alternatively, the biomass to be processed can be added directly to the microorganism or culture that has been induced to produce a biomass degrading enzyme.

A protein, e.g., an enzyme, e.g., an amylase or biomass degrading enzyme produced by the microorganism as described herein can also be separated or purified prior use in biomass processing. The protein, e.g., biomass degrading enzyme can be separated from one or more of the following components: the microorganism, e.g., the cells of the microorganism; the caramelized sugar product used to induce enzyme production, e.g., the caramelized sugar product that is remaining after enzyme induction; the inducer biomass used to induce enzyme production, e.g., the inducer biomass that is remaining after enzyme induction; components of the cell culture media, e.g., glucose, physiological salts; and one or more proteins present in the culture that do not have biomass degrading activity. The protein, e.g., biomass degrading enzyme can be purified, such that the biomass degrading enzyme is substantially free of other proteins that do not have biomass degrading activity, cell debris, nucleic acids, e.g., from the microorganism, caramelized sugar product, and/or inducer biomass. Methods for separation or purification of an enzyme are known in the art, and can include centrifugation, filtration, protein fractionation, size exclusion chromatography, affinity chromatography, or any combination thereof.

Converting Biomass into Products

The present invention provides methods and compositions for converting or processing a biomass into a product using a protein, e.g., an enzyme, e.g., an amylase or biomass degrading enzyme, wherein the protein, e.g., enzyme, e.g., amylase or biomass degrading enzyme is produced by contacting a microorganism with a composition comprising a caramelized sugar product, as described herein. Methods for converting a biomass to products, such as sugar products, are known in the art, for example, as described in US Patent Application 2014/0011258, the contents of which are incorporated by reference in its entirety. Briefly, a biomass is optimally pretreated, e.g., to reduce the recalcitrance, and saccharified by a saccharification process that involves incubating the treated biomass with biomass degrading or cellulolytic, enzymes to produce sugar products (e.g., glucose and/or xylose). The sugar products can then be further processed, e.g., by fermentation or distillation, to produce other products. Such products include alcohols (e.g., ethanol, isobutanol, or n-butanol), sugar alcohols (e.g., erythritol, xylitol, or sorbitol), or organic acids (e.g., lactic acid, pyruvic acid, succinic acid).

Products

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, cellobiose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids (e.g., lactic acid), hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives).

Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene).

Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols.

Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

In an embodiment, the product of the methods for converting a biomass provided herein, e.g., comprising using a protein, e.g., an enzyme, e.g., an amylase or biomass degrading enzyme produced as described herein, is a sugar product. In an embodiment, the sugar product is glucose. In an embodiment, the sugar product is xylose. In an embodiment, the sugar product is a mixture of glucose and xylose.

In an embodiment, the product of the methods for converting a biomass provided herein, e.g., comprising using a protein, e.g., an enzyme, e.g., an amylase or biomass degrading enzyme produced as described herein, is an organic acid product. In an embodiment, the organic acid product is lactic acid.

Biomass

The biomass to be processed using the methods described herein is a starchy material and/or a cellulosic material comprising cellulose, e.g., a lignocellulosic material. The biomass may also comprise hemicellulose and/or lignin. The biomass can comprise one or more of an agricultural product or waste, a paper product or waste, a forestry product, or a general waste, or any combination thereof. An agricultural product or waste comprises material that can be cultivated, harvested, or processed for use or consumption, e.g., by humans or animals, or any intermediate, byproduct, or waste that is generated from the cultivation, harvest, or processing methods. Agricultural products or waste include, but are not limited to, sugar cane, jute, hemp, flax, bamboo, sisal, alfalfa, hay, arracacha, buckwheat, banana, barley, cassava, kudzu, oca, sago, sorghum, potato, sweet potato, taro, yams, beans, favas, lentils, peas, grasses, switchgrass, *miscanthus*, cord grass, reed canary grass, grain residues, canola straw, wheat straw, barley straw, oat straw, rice straw, corn cobs, corn stover, corn fiber, coconut hair, beet pulp, bagasse, soybean stover, grain residues, rice hulls, oat hulls, wheat chaff, barley hulls, or beeswing, or a combination thereof. A paper product or waste comprises material that is used to make a paper product, any paper product, or any intermediate, byproduct or waste that is generated from making or breaking down the paper product. Paper products or waste include, but are not limited to, paper, pigmented papers, loaded papers, coated papers, corrugated paper, filled papers, magazines, printed matter, printer paper, polycoated paper, cardstock, cardboard, paperboard, or paper pulp, or a combination thereof. A forestry product or waste comprises material that is produced by cultivating, harvesting, or processing of wood, or any intermediate, byproduct, or waste that is generated from the cultivation, harvest, or processing of the wood. Forestry products or waste include, but are not limited to, aspen wood, wood from any genus or species of tree, particle board, wood chips, or sawdust, or a combination thereof. A general waste includes, but is not limited to, manure, sewage, or offal, or a combination thereof.

The biomass to be converted into products can be the same as the inducer biomass. Alternatively, the biomass to be converted into products is different than the inducer biomass.

In one embodiment, the biomass is treated prior to use in the process described herein. For example, the biomass is treated to reduce the recalcitrance of the biomass, to reduce its bulk density, and/or increase its surface area. Suitable biomass treatment process may include, but are not limited to: bombardment with electrons, sonication, oxidation, pyrolysis, steam explosion, chemical treatment, mechanical treatment, and freeze grinding. Preferably, the treatment method is bombardment with electrons.

In some embodiments, electron bombardment is performed until the biomass receives a total dose of at least 0.5 Mrad, e.g. at least 5, 10, 20, 30, or at least 40 Mrad. In some embodiments, the treatment is performed until the biomass receives a dose a of from about 0.5 Mrad to about 150 Mrad, about 1 Mrad to about 100 Mrad, about 5 Mrad to about 75 Mrad, about 2 Mrad to about 75 Mrad, about 10 Mrad to about 50 Mrad, e.g., about 5 Mrad to about 50 Mrad, about 20 Mrad to about 40 Mrad, about 10 Mrad to about 35 Mrad, or from about 20 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 9 Mrad/pass can in some cases cause thermal degradation of the feedstock material.

The biomass material (e.g., agricultural product or waste, paper product or waste, forestry product or waste, or general waste) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the biomass to a form that can be readily processed, the glucan- or xylan-containing cellulose in the biomass can be hydrolyzed to low molecular weight carbohydrates, such as sugars, by a saccharifying agent in a process referred to as saccharification. The saccharifying agent can comprise one or more enzymes, e.g., a biomass degrading enzyme, or acid, or a mixture thereof. The low molecular weight carbohydrates can then be used, for example, in an existing manufacturing plant, such as a single cell protein plant, an enzyme manufacturing plant, or a fuel plant, e.g., an ethanol manufacturing facility.

The biomass can be hydrolyzed using an enzyme, e.g., a biomass degrading enzyme, by combining the biomass material(s) and the enzyme in a solvent, e.g., in an aqueous solution. The enzymes can be induced and/or produced according to the methods described herein. In an embodiment, a biomass is hydrolyzed using a biomass degrading enzyme that has been produced by contacting a microorganism with a composition comprising a caramelized sugar product as described herein.

Specifically, the biomass degrading enzyme can be supplied by microorganisms that are capable of breaking down biomass (such as the cellulose and/or the lignin portions of the biomass), or that contain or manufacture various cellulolytic enzymes (cellulases), ligninases or various small molecule biomass degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate, e.g., of the biomass, can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Saccharification

The reduced-recalcitrance biomass is treated with the biomass degrading enzymes discussed above, generally by combining the reduced-recalcitrance biomass and a saccharifying agent, e.g., comprising one or more biomass degrading enzymes, in a fluid medium, e.g., an aqueous solution. In some cases, the biomass is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

Provided herein are methods and compositions for enhancing the production of a protein, e.g., an enzyme, e.g., an amylase or biomass degrading enzyme in a microorganism. The proteins, e.g., enzymes, e.g., amylases or biomass degrading enzyme(s) produced using the induction compositions and methods described herein can be used in the saccharification process as the saccharifying agent. The saccharifying agent is added directly to a biomass, e.g., a treated biomass, to initiate and perform the saccharification process to produce sugar products.

The saccharification agent may comprise the proteins, e.g., biomass degrading enzyme(s) produced using the induction compositions and methods described herein. The biomass degrading enzyme produced using the induction compositions and methods described herein can be a cellulase, a hemicellulase, or a ligninase. In an embodiment, the biomass degrading enzyme produced using the induction compositions and methods described herein can be one or more of the enzymes listed in Table 1. The saccharification agent may further comprise one or more additional agents that participate in the saccharification process, e.g., other proteins, e.g., enzymes, e.g., amylases or biomass degrading enzymes that were not obtained using the induction compositions or methods described herein.

In embodiments, the biomass is added to a culture comprising the microorganisms that have been induced to produce the proteins, e.g., enzymes, e.g., amylases or biomass degrading enzymes as described herein. Other saccharifying agents, e.g., proteins (e.g., biomass degrading enzymes) or acids, can be added to biomass and culture mixture for the saccharification process.

The saccharification process can be partially or completely performed in a tank (e.g., a tank having a volume of at least 4000 L, 40,000 L, 500,000 L, 2,000,000 L, 4,000,000 L, or 6,000,000 L or more) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

In a preferred embodiment, the saccharification reaction occurs at a pH optimal for the enzymatic reactions to occur, e.g., at the pH optimal for the activity of the biomass degrading enzymes. Preferably, the pH of the saccharification reaction is at pH 4-4.5. In a preferred embodiment, the saccharification reaction occurs at a temperature optimal for the enzymatic reactions to occur, e.g., at the temperature optimal for the activity of the biomass degrading enzymes. Preferably, the temperature of the saccharification reaction is at 42° C.-52° C.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 5%, 7.5%, 10%, 10.5%, or greater than 40%, or greater than 50, 60, 70, or even greater than 80% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 10,000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In the processes described herein, for example after saccharification, a sugar product (e.g., glucose and/or xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Further Processing

Further processing steps may be performed on the sugars produced by saccharification to produce alternative products. For example, the sugars can be hydrogenated, fermented, or treated with other chemicals to produce other products.

Glucose can be hydrogenated to sorbitol. Xylose can be hydrogenated to xylitol. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). The sorbitol and/or xylitol products can be isolated and purified using methods known in the art.

Sugar products from saccharification can also be fermented to produce alcohols, sugar alcohols, such as erythritol, or organic acids, e.g., lactic lacid, glutamic or citric acids or amino acids.

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic conditions can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in U.S. Prov. App. No. 61/579,559, filed Dec. 22, 2012, and U.S. Prov. App. No. 61/579,576, filed Dec. 22, 2012, the contents of both of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an algae. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

For instance, *Clostridium* spp. can be used to produce ethanol, butanol, butyric acid, acetic acid, and acetone. *Lactobacillus* spp. can be used to produce lactic acid.

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALK) (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other types of chemical transformation of the products from the processes described herein can be used, for example, production of organic sugar derived products such as (e.g., furfural and furfural-derived products). Chemical transformations of sugar derived products are described in U.S. Patent Publication No. 2014/0011248, filed Jul. 3, 2013, the disclosure of which is incorporated herein by reference in its entirety.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: General Methods

General materials and methods used for the examples described herein are provided.

Microorganisms and Culture Conditions

*T. reesei* strain RUTC30 (ATCC 56765) was used to produce cellulases. Spores ($>10^8$/ml) of *T. reesei* were inoculated into the seed culture media (Table 2 and 3) with 0.25% inoculation ratio at 30° C., shaken at 175 rpm.

TABLE 2

T. reesei seed culture media

| Chemical | Amount (gram or mL) |
|---|---|
| Corn Steep | 2 |
| Ammonium Sulfate | 1.4 |
| Potassium Hydroxide | 0.8 |
| Phthalic Acid | 5 |
| Lactose | 35 |
| Ammonium Hydroxide (6M) | Adjust pH to 6 |
| $CaCl_2$ | 0.3 |
| $MgSO_4$—$7H_2O$ | 0.3 |
| DI Water | 886.7 |
| Total (ml) | 939 |
| Autoclave | |
| After cooling | |
| 100X Antibiotics (1 g/L Acetoban), mL | 10 |
| Metal Solution (1000x), mL | 1 |
| 20X (60%) Glucose, mL | 50 |
| Total volume (mL) | 1000 |

TABLE 3

1000X metal solution

| Component | Amount (gram or mL) |
|---|---|
| $Fe(SO_4)$ $7H_2O$ (g) | 1 |
| $MnSO_4$ $7H_2O$ (g) | 0.32 |
| $ZnSO_4$ $7H_2O$ (g) | 0.28 |
| $CoCl_2$ $6H_2O$ (g) | 0.4 |
| 6N HCl | 0.2 |
| DI Water | 198 |
| Total (mL) | 200 |
| Filter sterilize | |

Seed culture was inoculated into the main culture media (Table 4) with 5% inoculation ratio. Main culture was conducted at 27° C., 700 rpm, 0.3 VVM in 3 L bioreactor (New Brunswick). pH was maintained at 3.8 with 6M $NH_4OH$. Culture period was 11 days.

TABLE 4

T. reesei enzyme production culture media

| Material | Amount (g/L) |
|---|---|
| Ammonium sulfate | 8 |
| Rice bran | 4 |
| Corncob or beeswing (35 mrad treated) | 80 |
| 6M $NH_4OH$ | Adjust to pH 6 |

Caramelized Sugar Preparation

Reagent grade glucose, maltose, and lactose were each used for making caramelized sugars. The caramelization reaction was carried out on stirred hot plates. 50% (w/v) sugar solution was prepared and pH was adjusted to 2.5 or 12 with HCl or NaOH, respectively. Temperature was maintained at 170° C. and the reaction time was 17 hours. Caramelized sugar (or sugar) was fed into the main culture in feeding rate of 4 to 5 g/L/day.

Analysis

Culture samples during the fermentation were taken from the main culture and analyzed by size exclusion chromatography (SEC)-HPLC for the determination of proteins. For cellulase activity assay, treated corncob was used for substrate of cellulase. Liberated glucose and xylose by cellulase produced in T. reesei culture were analyzed by HPLC.

Example 2: Caramelized Sugars Induce Cellulase Production

In this example, caramelized sugars are used to induce cellulose production in T. reesei. T. reesei was cultured and grown as described in the methods provided herein, e.g., Example 1. Caramelized glucose, maltose, and lactose was prepared according to the methods provided herein, e.g., Example 1.

Caramelized sugars, e.g., caramelized glucose, caramelized maltose, and caramelized lactose, (without cellulose inducer) were fed to a T. reesei culture at 5 g/L/day. Levels of protein produced (g/L) was measured at days 4, 6, 8, and 11 or 12. Without any sugar feeding, very little protein was produced (FIG. 1). Caramelized glucose, caramelized maltose, and caramelized lactose all induced protein production. Specifically, caramelized glucose and caramelized maltose showed higher induction capability than caramelized lactose. These results show that caramelized sugar was capable of inducing cellulase production.

Example 3: Analysis of the Composition of Caramelized Sugar

Reagent grade glucose, maltose, and lactose were each used for making caramelized sugars. The caramelization reaction was carried out on stirred hot plates. 50% (w/v) sugar solution was prepared and pH was adjusted to 2.5 or 12 with HCl or NaOH, respectively. Temperature was maintained at 170° C. and the reaction time was 17 hours.

Mass spectrometry analysis was performed to identify the components of caramelized glucose, caramelized maltose, and caramelized lactose. Caramelized sugar samples were diluted 1000-fold and analyzed by ESI-MS. Extracted ion chromatograms were generated from the TIC, stacked, and integrated.

Figure 2:
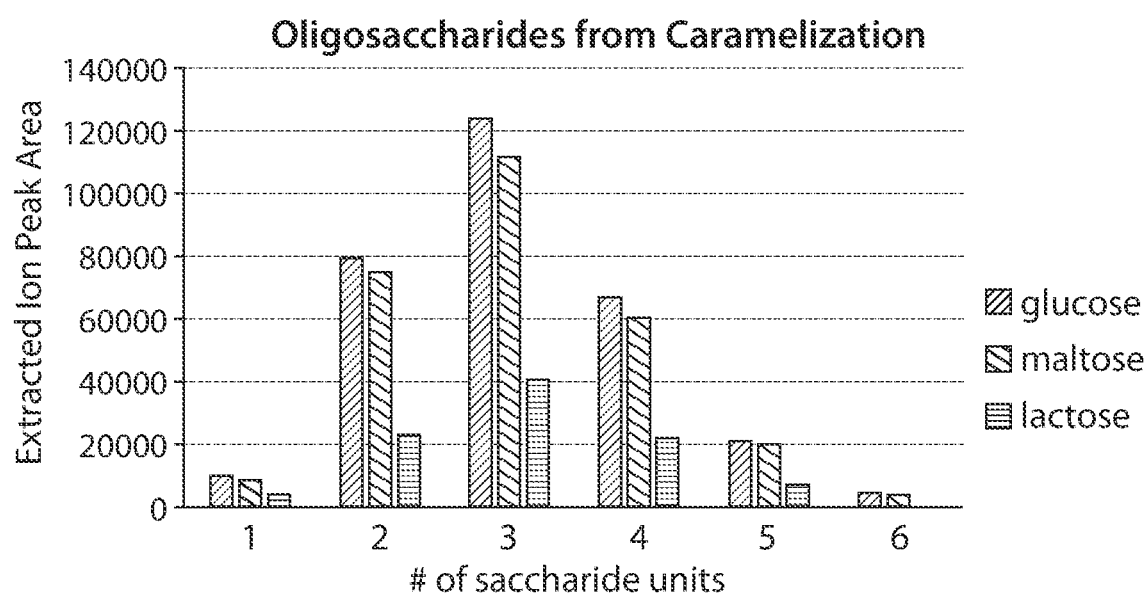
FIG. 2 is a graph showing the oligosaccharide composition of caramelized glucose, maltose, and lactose as determined by mass spectrometry. The number of saccharide units (2-6) is represented on the x-axis.

The results show that the caramelized sugar samples contain oligosaccharides (FIG. 2). Degree of polymerizations of oligosaccharides was in the range of 2 to 6, with trisaccharides being the most abundant species of oligosaccharides. In all three samples (caramelized glucose, caramelized maltose, and caramelized lactose), oligosaccharides up to at least pentasaccharides were observed, indicating that condensation reactions were taking place during the caramelization process. Some hydrolysis occurred as well, as indicated by the monosaccharide content in the caramelized maltose and caramelized lactose samples. The overall concentration of oligosaccharides in the caramelized lactose sample was the lowest compared to caramelized glucose and caramelized maltose. This data corresponds with the lower level of cellulase production measured after induction by caramelized lactose in T. reesei described in Example 2 (FIG. 1).

Example 4: Synergistic Effect of Caramelized Sugar with a Cellulose Inducer for Cellulase Production To assess the combined effect of cellulose inducer and caramelized sugar, cellulose inducers, e.g., corncob and beeswing, was added with caramelized sugar to a T. reesei culture, and cellulase production was measured by determining the resulting protein titer. T. reesei were cultured and induced to produce cellulase as described in Example 2.

Figure 3:
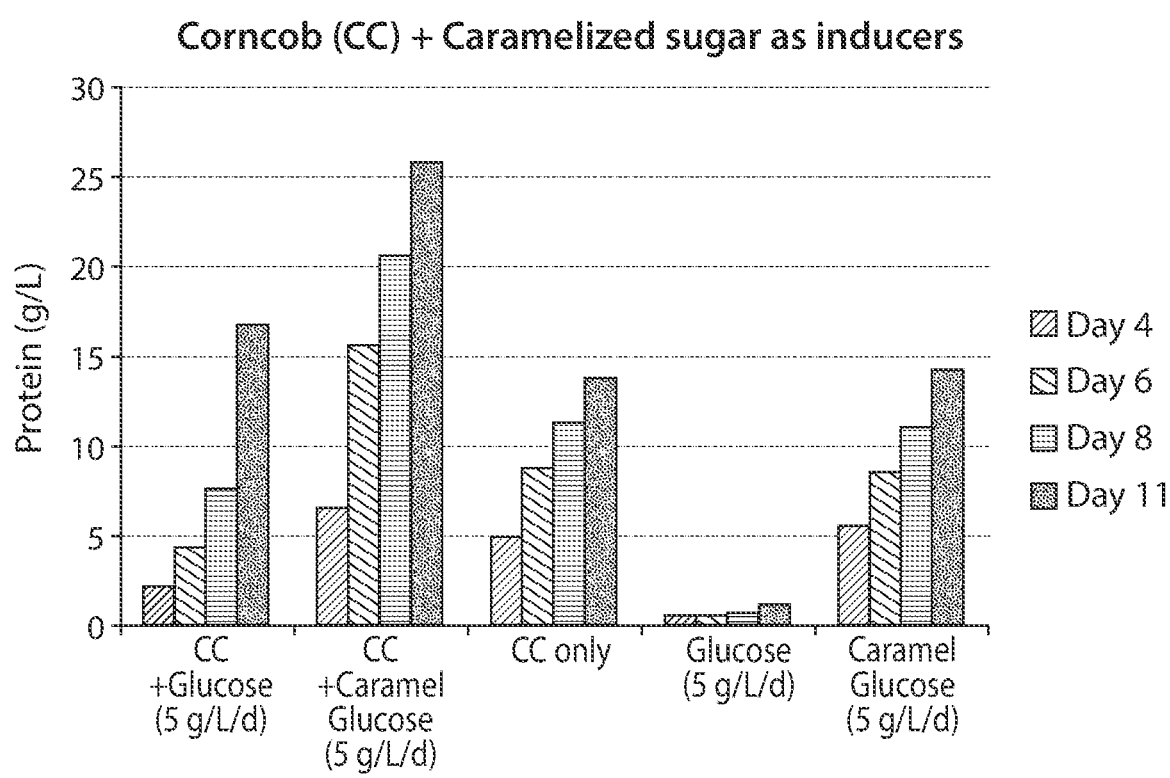
FIG. 3 is a graph showing the effect of the cellulose inducer corncob (CC) and caramelized sugar on the induction of cellulase production in *T. reesei*. Corncob alone (CC only), glucose that was not caramelized (glucose), caramelized glucose (caramel glucose), and combinations of corncob and glucose that was not caramelized (CC+glucose), and corncob and caramelized glucose (CC+caramel glucose) was fed to *T. reesei*. Cellulase production was measured by protein titer (g/L) at days 4, 6, 8 and 11, and represented on the y-axis.

Corncob and caramelized sugar was added together to a *T. reesei* culture. Induction by both cellulose inducer (corncob, CC) and caramelized sugar showed synergistic effect for cellulase production, as measured by protein titer (FIG. 3). Induction by corncob and caramelized glucose resulted in a 1.9 fold increase in protein titer, when compared to induction with corncob only (FIG. 3). Induction by corncob and caramelized glucose resulted in a 1.9 fold increase in protein titer, when compared to induction with caramelized sugar only (FIG. 3).

Adding glucose (not caramelized) to the corncob induction culture was also observed to help increase protein titer, but the effect was less than that observed from induction with caramelized glucose. As a negative control, glucose (not caramelized) was fed to the culture, and glucose-only feeding induced very little protein production, resulting in a low protein titer.

Figure 4:
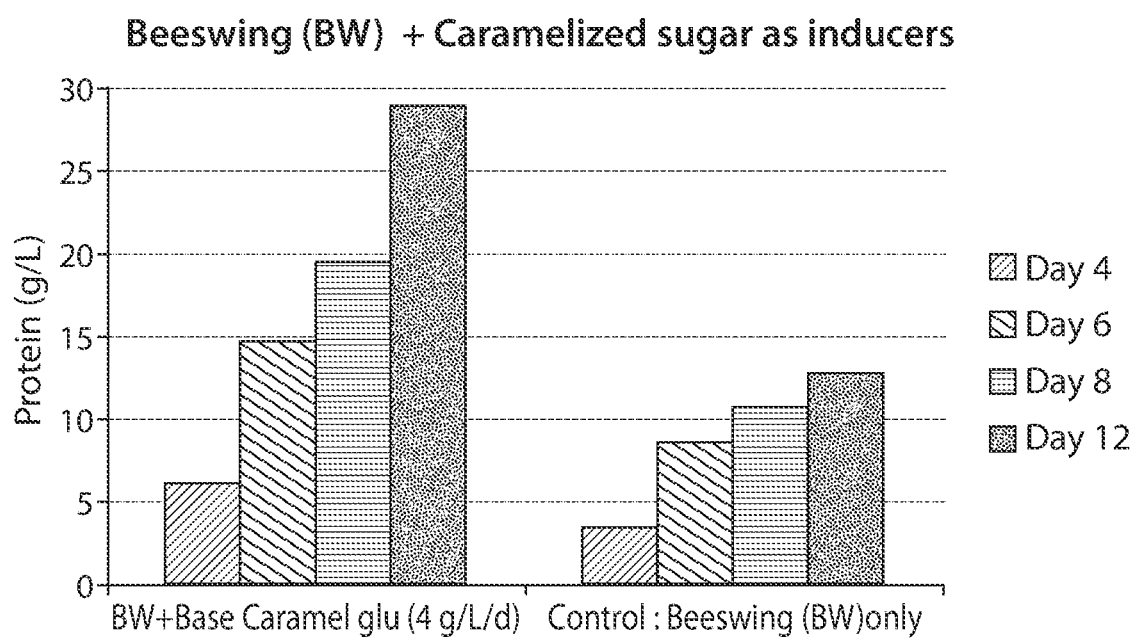
FIG. 4 is a graph showing the effect of the cellulose inducer beeswing (BW) and caramelized sugar on the induction of cellulase production in *T. reesei*. Beeswing only (BW) and the combination of beeswing and caramelized glucose (BW+Base Caramel glu) was fed to *T. reesei*. Cellulase production was measured by protein titer (g/L) at days 4, 6, 8 and 12, and represented on the y-axis.

A second cellulose inducer, beeswing, was next tested in combination with caramelized sugar generated in basic (pH 12) conditions. Synergistic effect of caramelized sugar with beeswing on cellulase production was also observed (FIG. 4). In this experiment, protein production was 2.3 fold higher when a combination of caramelized sugar and beeswing was used to induce production compared to the protein production observed using a single inducer, e.g., beeswing.

These results show that the combination of a caramelized sugar product and an inducer biomass, or cellulose inducer, further enhances the production of a biomass degrading enzyme in a microorganism.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method for inducing production of a cellobiase in a microorganism comprising:
   i) culturing the microorganism that produces the cellobiase in a cell culture;
   ii) providing a caramelized sugar composition comprising oligosaccharides, wherein trisaccharides are the most abundant oligosaccharides; and
   iii) contacting the cell culture with the caramelized sugar composition under conditions sufficient for production of the cellobiase;
thereby inducing production of the cellobiase.

2. The method of claim 1, wherein the cell culture is contacted with the caramelized sugar composition when the cell culture is free from sugar.

3. The method of claim 1, wherein the caramelized sugar composition is prepared by caramelizing glucose, xylose, maltose, lactose, or a combination thereof.

4. The method of claim 1, wherein the caramelized sugar composition further comprises dehydration products of the oligosaccharides, hydration products of the oligosaccharides, disproportionation products of the oligosaccharides, colored aromatic products, or any combination thereof.

5. The method of claim 1, further comprising contacting the cell culture with an inducer biomass.

6. The method of claim 1, wherein the caramelized sugar composition further comprises cellobiose, β-cellobiono-1,5-lactone, lactose, D-xylose, xylobiose, galactose, and/or sophorose.

7. The method of claim 1, wherein the microorganism that produces the cellobiase is from a species in the genera selected from *Bacillus, Coprinus, Myceliophthora, Cephalosporium, Scytalidium, Penicillium, Aspergillus, Pseudomonas, Humicola, Fusarium, Thielavia, Acremonium, Chrysosporium* or *Trichoderma*.

8. The method of claim 1, further comprising separating the cellobiase from a component of the cell culture.

9. The method of claim 1, wherein the microorganism that produces the cellobiase is from a species in the genera *Trichoderma*.

10. The method of claim 1, wherein the microorganism that produces the cellobiase is *T. reesei* or a variant thereof.

11. The method of claim 1, wherein the microorganism that produces the cellobiase is selected from *T. reesei* QM6a, *T. reesei* RL-P37, *T. reesei* MCG-80, *T. reesei* RUTC30, *T. reesei* RUT-NG14, *T. reesei* PC3-7, and *T. reesei* QM9414.

12. The method of claim 1, wherein the microorganism that produces the cellobiase is *T. reesei* RUTC30.

13. The method of claim 1, wherein the cellobiase is Cel3a.

14. The method of claim 13, wherein the Cel3a comprises the amino acid sequence of SEQ ID NO: 5, or an amino acid sequence with at least 90% identity to SEQ ID NO: 5.

15. The method of claim 13, wherein the Cel3a comprises the amino acid sequence of SEQ ID NO: 5, or an amino acid sequence with at least 95% identity to SEQ ID NO: 5.

16. The method of claim 13, wherein the Cel3a comprises the amino acid sequence of SEQ ID NO: 5.

17. The method of claim 5, wherein the caramelized sugar composition and the inducer biomass are added to the cell culture simultaneously.

18. The method of claim 5, wherein the caramelized sugar composition and the inducer biomass are added to the cell culture sequentially.

19. A method for inducing production of a Cel3a enzyme in a microorganism comprising:

i) culturing the microorganism that produces the Cel3a enzyme in a cell culture;
ii) providing a caramelized sugar composition comprising oligosaccharides, wherein trisaccharides are the most abundant oligosaccharides; and
iii) cooling the caramelized sugar composition; and
iv) contacting the cell culture with the caramelized sugar composition thereby inducing production of the Cel3a enzyme.

20. The method of claim 1, wherein the caramelized sugar composition is prepared by enzymatically saccharifying a biomass to obtain a saccharified biomass composition and caramelizing the saccharified biomass composition.

21. The method of claim 19, wherein the caramelized sugar composition is prepared by enzymatically saccharifying a biomass to obtain a saccharified biomass composition and caramelizing the saccharified biomass composition.

\* \* \* \* \*

SEQUENCE LISTING

```
<160> NUMBER OF SEQ ID NOS: 15

<210> SEQ ID NO 1
<211> LENGTH: 800
<212> TYPE: PRT
<213> ORGANISM: Podospora anserina

<400> SEQUENCE: 1

Met Lys Ser Ser Val Phe Trp Gly Ala Ser Leu Thr Ser Ala Val Val
1               5                   10                  15

Arg Ala Ile Asp Leu Pro Phe Gln Phe Tyr Pro Asn Cys Val Asp Asp
                20                  25                  30

Leu Leu Ser Thr Asn Gln Val Cys Asn Thr Thr Leu Ser Pro Pro Glu
            35                  40                  45

Arg Ala Ala Ala Leu Val Ala Ala Leu Thr Pro Glu Glu Lys Leu Gln
        50                  55                  60

Asn Ile Val Ser Lys Ser Leu Gly Ala Pro Arg Ile Gly Leu Pro Ala
65                  70                  75                  80

Tyr Asn Trp Trp Ser Glu Ala Leu His Gly Val Ala Tyr Ala Pro Gly
                85                  90                  95

Thr Gln Phe Trp Gln Gly Asp Gly Pro Phe Asn Ser Ser Thr Ser Phe
            100                 105                 110

Pro Met Pro Leu Leu Met Ala Ala Thr Phe Asp Asp Glu Leu Leu Glu
        115                 120                 125

Lys Ile Ala Glu Val Ile Gly Ile Glu Gly Arg Ala Phe Gly Asn Ala
    130                 135                 140

Gly Phe Ser Gly Leu Asp Tyr Trp Thr Pro Asn Val Asn Pro Phe Lys
145                 150                 155                 160

Asp Pro Arg Trp Gly Arg Gly Ser Glu Thr Pro Gly Glu Asp Val Leu
                165                 170                 175

Leu Val Lys Arg Tyr Ala Ala Ala Met Ile Lys Gly Leu Glu Gly Pro
            180                 185                 190

Val Pro Glu Lys Glu Arg Arg Val Val Ala Thr Cys Lys His Tyr Ala
        195                 200                 205

Ala Asn Asp Phe Glu Asp Trp Asn Gly Ala Thr Arg His Asn Phe Asn
    210                 215                 220
```

```
Ala Lys Ile Ser Leu Gln Asp Met Ala Glu Tyr Tyr Phe Met Pro Phe
225                 230                 235                 240

Gln Gln Cys Val Arg Asp Ser Arg Val Gly Ser Ile Met Cys Ala Tyr
                245                 250                 255

Asn Ala Val Asn Gly Val Pro Ser Cys Ala Ser Pro Tyr Leu Leu Gln
            260                 265                 270

Thr Ile Leu Arg Glu His Trp Asn Trp Thr Glu His Asn Asn Tyr Ile
        275                 280                 285

Thr Ser Asp Cys Glu Ala Val Leu Asp Val Ser Leu Asn His Lys Tyr
    290                 295                 300

Ala Ala Thr Asn Ala Glu Gly Thr Ala Ile Ser Phe Glu Ala Gly Met
305                 310                 315                 320

Asp Thr Ser Cys Glu Tyr Glu Gly Ser Ser Asp Ile Pro Gly Ala Trp
                325                 330                 335

Ser Gln Gly Leu Leu Lys Glu Ser Thr Val Asp Arg Ala Leu Leu Arg
            340                 345                 350

Leu Tyr Glu Gly Ile Val Arg Ala Gly Tyr Phe Asp Gly Lys Gln Ser
        355                 360                 365

Leu Tyr Ser Ser Leu Gly Trp Ala Asp Val Asn Lys Pro Ser Ala Gln
    370                 375                 380

Lys Leu Ser Leu Gln Ala Ala Val Asp Gly Thr Val Leu Leu Lys Asn
385                 390                 395                 400

Asp Gly Thr Leu Pro Leu Ser Asp Leu Leu Asp Lys Ser Arg Pro Lys
                405                 410                 415

Lys Val Ala Met Ile Gly Phe Trp Ser Asp Ala Lys Asp Lys Leu Arg
            420                 425                 430

Gly Gly Tyr Ser Gly Thr Ala Ala Tyr Leu His Thr Pro Ala Tyr Ala
        435                 440                 445

Ala Ser Gln Leu Gly Ile Pro Phe Ser Thr Ala Ser Gly Pro Ile Leu
    450                 455                 460

His Ser Asp Leu Ala Ser Asn Gln Ser Trp Thr Asp Asn Ala Met Ala
465                 470                 475                 480

Ala Ala Lys Asp Ala Asp Tyr Ile Leu Tyr Phe Gly Gly Ile Asp Thr
                485                 490                 495

Ser Ala Ala Gly Glu Thr Lys Asp Arg Tyr Asp Leu Asp Trp Pro Gly
            500                 505                 510

Ala Gln Leu Ser Leu Ile Asn Leu Leu Thr Thr Leu Ser Lys Pro Leu
        515                 520                 525

Ile Val Leu Gln Met Gly Asp Gln Leu Asp Asn Thr Pro Leu Leu Ser
    530                 535                 540

Asn Pro Lys Ile Asn Ala Ile Leu Trp Ala Asn Trp Pro Gly Gln Asp
545                 550                 555                 560

Gly Gly Thr Ala Val Met Glu Leu Val Thr Gly Leu Lys Ser Pro Ala
                565                 570                 575

Gly Arg Leu Pro Val Thr Gln Tyr Pro Ser Asn Phe Thr Glu Leu Val
            580                 585                 590

Pro Met Thr Asp Met Ala Leu Arg Pro Ser Ala Gly Asn Ser Gln Leu
        595                 600                 605

Gly Arg Thr Tyr Arg Trp Tyr Lys Thr Pro Val Gln Ala Phe Gly Phe
    610                 615                 620

Gly Leu His Tyr Thr Thr Phe Ser Pro Lys Phe Gly Lys Lys Phe Pro
625                 630                 635                 640

Ala Val Ile Asp Val Asp Glu Val Leu Glu Gly Cys Asp Asp Lys Tyr
```

```
              645                 650                 655
Leu Asp Thr Cys Pro Leu Pro Asp Leu Pro Val Val Glu Asn Arg
            660                 665                 670

Gly Asn Arg Thr Ser Asp Tyr Val Ala Leu Ala Phe Val Ser Ala Pro
            675                 680                 685

Gly Val Gly Pro Gly Pro Trp Pro Ile Lys Thr Leu Gly Ala Phe Thr
690                 695                 700

Arg Leu Arg Gly Val Lys Gly Glu Lys Arg Glu Gly Gly Leu Lys
705                 710                 715                 720

Trp Asn Leu Gly Asn Leu Ala Arg His Asp Glu Gly Asn Thr Val
            725                 730                 735

Val Tyr Pro Gly Lys Tyr Glu Val Ser Leu Asp Glu Pro Pro Lys Ala
            740                 745                 750

Arg Leu Arg Phe Glu Ile Val Arg Gly Lys Gly Lys Gly Lys Val
            755                 760                 765

Lys Gly Lys Gly Lys Ala Ala Gln Lys Gly Gly Val Val Leu Asp Arg
770                 775                 780

Trp Pro Lys Pro Pro Lys Gly Gln Glu Pro Pro Ala Ile Glu Arg Val
785                 790                 795                 800

<210> SEQ ID NO 2
<211> LENGTH: 316
<212> TYPE: PRT
<213> ORGANISM: Trichoderma reesei

<400> SEQUENCE: 2

Met Val Arg Arg Thr Ala Leu Leu Ala Leu Gly Ala Leu Ser Thr Leu
1               5                   10                  15

Ser Met Ala Gln Ile Ser Asp Asp Phe Glu Ser Gly Trp Asp Gln Thr
            20                  25                  30

Lys Trp Pro Ile Ser Ala Pro Asp Cys Asn Gln Gly Gly Thr Val Ser
        35                  40                  45

Leu Asp Thr Thr Val Ala His Ser Gly Ser Asn Ser Met Lys Val Val
50                  55                  60

Gly Gly Pro Asn Gly Tyr Cys Gly His Ile Phe Phe Gly Thr Thr Gln
65                  70                  75                  80

Val Pro Thr Gly Asp Val Tyr Val Arg Ala Trp Ile Arg Leu Gln Thr
                85                  90                  95

Ala Leu Gly Ser Asn His Val Thr Phe Ile Ile Met Pro Asp Thr Ala
            100                 105                 110

Gln Gly Gly Lys His Leu Arg Ile Gly Gly Gln Ser Gln Val Leu Asp
        115                 120                 125

Tyr Asn Arg Glu Ser Asp Asp Ala Thr Leu Pro Asp Leu Ser Pro Asn
130                 135                 140

Gly Ile Ala Ser Thr Val Thr Leu Pro Thr Gly Ala Phe Gln Cys Phe
145                 150                 155                 160

Glu Tyr His Leu Gly Thr Asp Gly Thr Ile Glu Thr Trp Leu Asn Gly
                165                 170                 175

Ser Leu Ile Pro Gly Met Thr Val Gly Pro Gly Val Asp Asn Pro Asn
            180                 185                 190

Asp Ala Gly Trp Thr Arg Ala Ser Tyr Ile Pro Glu Ile Thr Gly Val
        195                 200                 205

Asn Phe Gly Trp Glu Ala Tyr Ser Gly Asp Val Asn Thr Val Trp Phe
210                 215                 220
```

```
Asp Asp Ile Ser Ile Ala Ser Thr Arg Val Gly Cys Gly Pro Gly Ser
225                 230                 235                 240

Pro Gly Gly Pro Gly Ser Ser Thr Gly Arg Ser Ser Thr Ser Gly
            245                 250                 255

Pro Thr Ser Thr Ser Arg Pro Ser Thr Thr Ile Pro Pro Thr Ser
            260                 265                 270

Arg Thr Thr Thr Ala Thr Gly Pro Thr Gln Thr His Tyr Gly Gln Cys
        275                 280                 285

Gly Gly Ile Gly Tyr Ser Gly Pro Thr Val Cys Ala Ser Gly Thr Thr
    290                 295                 300

Cys Gln Val Leu Asn Pro Tyr Tyr Ser Gln Cys Leu
305                 310                 315

<210> SEQ ID NO 3
<211> LENGTH: 460
<212> TYPE: PRT
<213> ORGANISM: Trichoderma reesei

<400> SEQUENCE: 3

Met Ala Ser Arg Phe Phe Ala Leu Leu Leu Ala Ile Pro Ile Gln
1               5                   10                  15

Ala Gln Ser Pro Val Trp Gly Gln Cys Gly Gly Ile Gly Trp Ser Gly
            20                  25                  30

Pro Thr Thr Cys Val Gly Gly Ala Thr Cys Val Ser Tyr Asn Pro Tyr
        35                  40                  45

Tyr Ser Gln Cys Ile Pro Ser Thr Gln Ala Ser Ser Ile Ala Ser
    50                  55                  60

Thr Thr Leu Val Thr Ser Phe Thr Thr Thr Ala Thr Arg Thr Ser
65                  70                  75                  80

Ala Ser Thr Pro Pro Ala Ser Ser Gly Ala Gly Gly Ala Thr Cys
                85                  90                  95

Ser Ala Leu Pro Gly Ser Ile Thr Leu Arg Ser Asn Ala Lys Leu Asn
                100                 105                 110

Asp Leu Phe Thr Met Phe Asn Gly Asp Lys Val Thr Thr Lys Asp Lys
            115                 120                 125

Phe Ser Cys Arg Gln Ala Glu Met Ser Glu Leu Ile Gln Arg Tyr Glu
130                 135                 140

Leu Gly Thr Leu Pro Gly Arg Pro Ser Thr Leu Thr Ala Ser Phe Ser
145                 150                 155                 160

Gly Asn Thr Leu Thr Ile Asn Cys Gly Glu Ala Gly Lys Ser Ile Ser
                165                 170                 175

Phe Thr Val Thr Ile Thr Tyr Pro Ser Ser Gly Thr Ala Pro Tyr Pro
            180                 185                 190

Ala Ile Ile Gly Tyr Gly Gly Gly Ser Leu Pro Ala Pro Ala Gly Val
        195                 200                 205

Ala Met Ile Asn Phe Asn Asn Asp Asn Ile Ala Ala Gln Val Asn Thr
    210                 215                 220

Gly Ser Arg Gly Gln Gly Lys Phe Tyr Asp Leu Tyr Gly Ser Ser His
225                 230                 235                 240

Ser Ala Gly Ala Met Thr Ala Trp Ala Trp Gly Val Ser Arg Val Ile
                245                 250                 255

Asp Ala Leu Glu Leu Val Pro Gly Ala Arg Ile Asp Thr Thr Lys Ile
            260                 265                 270

Gly Val Thr Gly Cys Ser Arg Asn Gly Lys Gly Ala Met Val Ala Gly
        275                 280                 285
```

```
Ala Phe Glu Lys Arg Ile Val Leu Thr Leu Pro Gln Glu Ser Gly Ala
        290                 295                 300

Gly Gly Ser Ala Cys Trp Arg Ile Ser Asp Tyr Leu Lys Ser Gln Gly
305                 310                 315                 320

Ala Asn Ile Gln Thr Ala Ser Glu Ile Ile Gly Glu Asp Pro Trp Phe
                325                 330                 335

Ser Thr Thr Phe Asn Ser Tyr Val Asn Gln Val Pro Val Leu Pro Phe
            340                 345                 350

Asp His His Ser Leu Ala Ala Leu Ile Ala Pro Arg Gly Leu Phe Val
        355                 360                 365

Ile Asp Asn Asn Ile Asp Trp Leu Gly Pro Gln Ser Cys Phe Gly Cys
    370                 375                 380

Met Thr Ala Ala His Met Ala Trp Gln Ala Leu Gly Val Ser Asp His
385                 390                 395                 400

Met Gly Tyr Ser Gln Ile Gly Ala His Ala His Cys Ala Phe Pro Ser
                405                 410                 415

Asn Gln Gln Ser Gln Leu Thr Ala Phe Val Gln Lys Phe Leu Leu Gly
            420                 425                 430

Gln Ser Thr Asn Thr Ala Ile Phe Gln Ser Asp Phe Ser Ala Asn Gln
        435                 440                 445

Ser Gln Trp Ile Asp Trp Thr Thr Pro Thr Leu Ser
    450                 455                 460

<210> SEQ ID NO 4
<211> LENGTH: 466
<212> TYPE: PRT
<213> ORGANISM: Trichoderma reesei

<400> SEQUENCE: 4

Met Leu Pro Lys Asp Phe Gln Trp Gly Phe Ala Thr Ala Ala Tyr Gln
1               5                   10                  15

Ile Glu Gly Ala Val Asp Gln Asp Gly Arg Gly Pro Ser Ile Trp Asp
            20                  25                  30

Thr Phe Cys Ala Gln Pro Gly Lys Ile Ala Asp Gly Ser Ser Gly Val
        35                  40                  45

Thr Ala Cys Asp Ser Tyr Asn Arg Thr Ala Glu Asp Ile Ala Leu Leu
    50                  55                  60

Lys Ser Leu Gly Ala Lys Ser Tyr Arg Phe Ser Ile Ser Trp Ser Arg
65                  70                  75                  80

Ile Ile Pro Glu Gly Gly Arg Gly Asp Ala Val Asn Gln Ala Gly Ile
                85                  90                  95

Asp His Tyr Val Lys Phe Val Asp Asp Leu Leu Asp Ala Gly Ile Thr
            100                 105                 110

Pro Phe Ile Thr Leu Phe His Trp Asp Leu Pro Glu Gly Leu His Gln
        115                 120                 125

Arg Tyr Gly Gly Leu Leu Asn Arg Thr Glu Phe Pro Leu Asp Phe Glu
    130                 135                 140

Asn Tyr Ala Arg Val Met Phe Arg Ala Leu Pro Lys Val Arg Asn Trp
145                 150                 155                 160

Ile Thr Phe Asn Glu Pro Leu Cys Ser Ala Ile Pro Gly Tyr Gly Ser
                165                 170                 175

Gly Thr Phe Ala Pro Gly Arg Gln Ser Thr Ser Glu Pro Trp Thr Val
            180                 185                 190

Gly His Asn Ile Leu Val Ala His Gly Arg Ala Val Lys Ala Tyr Arg
```

```
                195                 200                 205
Asp Asp Phe Lys Pro Ala Ser Gly Asp Gly Gln Ile Gly Ile Val Leu
    210                 215                 220
Asn Gly Asp Phe Thr Tyr Pro Trp Asp Ala Ala Asp Pro Ala Asp Lys
225                 230                 235                 240
Glu Ala Ala Glu Arg Leu Glu Phe Phe Thr Ala Trp Phe Ala Asp
                245                 250                 255
Pro Ile Tyr Leu Gly Asp Tyr Pro Ala Ser Met Arg Lys Gln Leu Gly
                260                 265                 270
Asp Arg Leu Pro Thr Phe Thr Pro Glu Glu Arg Ala Leu Val His Gly
            275                 280                 285
Ser Asn Asp Phe Tyr Gly Met Asn His Tyr Thr Ser Asn Tyr Ile Arg
    290                 295                 300
His Arg Ser Ser Pro Ala Ser Ala Asp Asp Thr Val Gly Asn Val Asp
305                 310                 315                 320
Val Leu Phe Thr Asn Lys Gln Gly Asn Cys Ile Gly Pro Glu Thr Gln
                325                 330                 335
Ser Pro Trp Leu Arg Pro Cys Ala Ala Gly Phe Arg Asp Phe Leu Val
            340                 345                 350
Trp Ile Ser Lys Arg Tyr Gly Tyr Pro Pro Ile Tyr Val Thr Glu Asn
    355                 360                 365
Gly Thr Ser Ile Lys Gly Glu Ser Asp Leu Pro Lys Glu Lys Ile Leu
    370                 375                 380
Glu Asp Asp Phe Arg Val Lys Tyr Tyr Asn Glu Tyr Ile Arg Ala Met
385                 390                 395                 400
Val Thr Ala Val Glu Leu Asp Gly Val Asn Val Lys Gly Tyr Phe Ala
                405                 410                 415
Trp Ser Leu Met Asp Asn Phe Glu Trp Ala Asp Gly Tyr Val Thr Arg
            420                 425                 430
Phe Gly Val Thr Tyr Val Asp Tyr Glu Asn Gly Gln Lys Arg Phe Pro
            435                 440                 445
Lys Lys Ser Ala Lys Ser Leu Lys Pro Leu Phe Asp Glu Leu Ile Ala
    450                 455                 460
Ala Ala
465

<210> SEQ ID NO 5
<211> LENGTH: 744
<212> TYPE: PRT
<213> ORGANISM: Trichoderma reesei

<400> SEQUENCE: 5

Met Arg Tyr Arg Thr Ala Ala Ala Leu Ala Leu Ala Thr Gly Pro Phe
1               5                   10                  15
Ala Arg Ala Asp Ser His Ser Thr Ser Gly Ala Ser Ala Glu Ala Val
            20                  25                  30
Val Pro Pro Ala Gly Thr Pro Trp Gly Thr Ala Tyr Asp Lys Ala Lys
        35                  40                  45
Ala Ala Leu Ala Lys Leu Asn Leu Gln Asp Lys Val Gly Ile Val Ser
    50                  55                  60
Gly Val Gly Trp Asn Gly Gly Pro Cys Val Gly Asn Thr Ser Pro Ala
65                  70                  75                  80
Ser Lys Ile Ser Tyr Pro Ser Leu Cys Leu Gln Asp Gly Pro Leu Gly
                85                  90                  95
```

-continued

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val

```
            515                 520                 525
Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Lys Gln Leu Arg Gly Phe Ala Lys Leu
        675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 6
<211> LENGTH: 418
<212> TYPE: PRT
<213> ORGANISM: Trichoderma reesei

<400> SEQUENCE: 6

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140
```

```
Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
            165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
            245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
            325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
            405                 410                 415

Arg Lys

<210> SEQ ID NO 7
<211> LENGTH: 471
<212> TYPE: PRT
<213> ORGANISM: Trichoderma reesei

<400> SEQUENCE: 7

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
                85                  90                  95
```

```
Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 8
<211> LENGTH: 514
<212> TYPE: PRT
<213> ORGANISM: Trichoderma reesei

<400> SEQUENCE: 8
```

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
    115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415
```

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu

<210> SEQ ID NO 9
<211> LENGTH: 459
<212> TYPE: PRT
<213> ORGANISM: Trichoderma reesei

<400> SEQUENCE: 9

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

```
Ile Ile Thr Gln Phe Asn Thr Asp Asn Gly Ser Pro Ser Gly Asn Leu
            275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
                340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
                420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
            450                 455

<210> SEQ ID NO 10
<211> LENGTH: 234
<212> TYPE: PRT
<213> ORGANISM: Trichoderma reesei

<400> SEQUENCE: 10

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190
```

```
Asn Tyr Leu Arg Asp Asn Lys Gly Tyr Asn Ala Ala Gly Gln Tyr Val
            195                 200                 205

Leu Ser Tyr Gln Phe Gly Thr Glu Pro Phe Thr Gly Ser Gly Thr Leu
            210                 215                 220

Asn Val Ala Ser Trp Thr Ala Ser Ile Asn
225                 230

<210> SEQ ID NO 11
<211> LENGTH: 242
<212> TYPE: PRT
<213> ORGANISM: Trichoderma reesei

<400> SEQUENCE: 11

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro

<210> SEQ ID NO 12
<211> LENGTH: 838
<212> TYPE: PRT
<213> ORGANISM: Trichoderma reesei

<400> SEQUENCE: 12

Met Lys Val Ser Arg Val Leu Ala Leu Val Leu Gly Ala Val Ile Pro
1               5                   10                  15

Ala His Ala Phe Ser Trp Lys Asn Val Lys Leu Gly Gly Gly Gly
            20                  25                  30
```

```
Gly Phe Val Pro Gly Ile Ile Phe His Pro Lys Thr Lys Gly Val Ala
            35                  40                  45

Tyr Ala Arg Thr Asp Ile Gly Gly Leu Tyr Arg Leu Asn Ala Asp Asp
 50                  55                  60

Ser Trp Thr Ala Val Thr Asp Gly Ile Ala Asp Asn Ala Gly Trp His
 65                  70                  75                  80

Asn Trp Gly Ile Asp Ala Val Ala Leu Asp Pro Gln Asp Asp Gln Lys
                 85                  90                  95

Val Tyr Ala Ala Val Gly Met Tyr Thr Asn Ser Trp Asp Pro Ser Asn
                100                 105                 110

Gly Ala Ile Ile Arg Ser Ser Asp Arg Gly Ala Thr Trp Ser Phe Thr
            115                 120                 125

Asn Leu Pro Phe Lys Val Gly Gly Asn Met Pro Gly Arg Gly Ala Gly
130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190

Pro Ser Asp Ser Asn Gly Tyr Asn Ser Asp Lys Gln Gly Leu Met Trp
            195                 200                 205

Val Thr Phe Asp Ser Thr Ser Ser Thr Gly Gly Ala Thr Ser Arg
            210                 215                 220

Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
                245                 250                 255

Tyr Phe Pro His Lys Ala Lys Leu Gln Pro Ala Glu Lys Ala Leu Tyr
            260                 265                 270

Leu Thr Tyr Ser Asp Gly Thr Gly Pro Tyr Asp Gly Thr Leu Gly Ser
            275                 280                 285

Val Trp Arg Tyr Asp Ile Ala Gly Gly Thr Trp Lys Asp Ile Thr Pro
290                 295                 300

Val Ser Gly Ser Asp Leu Tyr Phe Gly Phe Gly Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
            340                 345                 350

Pro Ile Trp Ala Trp Ala Ser Tyr Pro Thr Glu Thr Tyr Tyr Tyr Ser
            355                 360                 365

Ile Ser Thr Pro Lys Ala Pro Trp Ile Lys Asn Asn Phe Ile Asp Val
            370                 375                 380

Thr Ser Glu Ser Pro Ser Asp Gly Leu Ile Lys Arg Leu Gly Trp Met
385                 390                 395                 400

Ile Glu Ser Leu Glu Ile Asp Pro Thr Asp Ser Asn His Trp Leu Tyr
                405                 410                 415

Gly Thr Gly Met Thr Ile Phe Gly Gly His Asp Leu Thr Asn Trp Asp
            420                 425                 430

Thr Arg His Asn Val Ser Ile Gln Ser Leu Ala Asp Gly Ile Glu Glu
            435                 440                 445

Phe Ser Val Gln Asp Leu Ala Ser Ala Pro Gly Gly Ser Glu Leu Leu
```

```
                  450                 455                 460
Ala Ala Val Gly Asp Asp Asn Gly Phe Thr Phe Ala Ser Arg Asn Asp
465                 470                 475                 480

Leu Gly Thr Ser Pro Gln Thr Val Trp Ala Thr Pro Thr Trp Ala Thr
                    485                 490                 495

Ser Thr Ser Val Asp Tyr Ala Gly Asn Ser Val Lys Ser Val Val Arg
                500                 505                 510

Val Gly Asn Thr Ala Gly Thr Gln Gln Val Ala Ile Ser Ser Asp Gly
            515                 520                 525

Gly Ala Thr Trp Ser Ile Asp Tyr Ala Ala Asp Thr Ser Met Asn Gly
            530                 535                 540

Gly Thr Val Ala Tyr Ser Ala Asp Gly Asp Thr Ile Leu Trp Ser Thr
545                 550                 555                 560

Ala Ser Ser Gly Val Gln Arg Ser Gln Phe Gln Gly Ser Phe Ala Ser
                565                 570                 575

Val Ser Ser Leu Pro Ala Gly Ala Val Ile Ala Ser Asp Lys Lys Thr
            580                 585                 590

Asn Ser Val Phe Tyr Ala Gly Ser Gly Ser Thr Phe Tyr Val Ser Lys
            595                 600                 605

Asp Thr Gly Ser Ser Phe Thr Arg Gly Pro Lys Leu Gly Ser Ala Gly
        610                 615                 620

Thr Ile Arg Asp Ile Ala Ala His Pro Thr Thr Ala Gly Thr Leu Tyr
625                 630                 635                 640

Val Ser Thr Asp Val Gly Ile Phe Arg Ser Thr Asp Ser Gly Thr Thr
                645                 650                 655

Phe Gly Gln Val Ser Thr Ala Leu Thr Asn Thr Tyr Gln Ile Ala Leu
            660                 665                 670

Gly Val Gly Ser Gly Ser Asn Trp Asn Leu Tyr Ala Phe Gly Thr Gly
            675                 680                 685

Pro Ser Gly Ala Arg Leu Tyr Ala Ser Gly Asp Ser Gly Ala Ser Trp
        690                 695                 700

Thr Asp Ile Gln Gly Ser Gln Gly Phe Gly Ser Ile Asp Ser Thr Lys
705                 710                 715                 720

Val Ala Gly Ser Gly Ser Thr Ala Gly Gln Val Tyr Val Gly Thr Asn
                725                 730                 735

Gly Arg Gly Val Phe Tyr Ala Gln Gly Thr Val Gly Gly Thr Gly
            740                 745                 750

Gly Thr Ser Ser Ser Thr Lys Gln Ser Ser Ser Thr Ser Ser Ala
            755                 760                 765

Ser Ser Ser Thr Thr Leu Arg Ser Val Val Ser Thr Thr Arg Ala
        770                 775                 780

Ser Thr Val Thr Ser Ser Arg Thr Ser Ser Ala Ala Gly Pro Thr Gly
785                 790                 795                 800

Ser Gly Val Ala Gly His Tyr Ala Gln Cys Gly Gly Ile Gly Trp Thr
                805                 810                 815

Gly Pro Thr Gln Cys Val Ala Pro Tyr Val Cys Gln Lys Gln Asn Asp
            820                 825                 830

Tyr Tyr Tyr Gln Cys Val
            835

<210> SEQ ID NO 13
<211> LENGTH: 373
<212> TYPE: PRT
<213> ORGANISM: Podospora anserina
```

<400> SEQUENCE: 13

Met Lys Gly Leu Phe Ala Phe Gly Leu Gly Leu Leu Ser Leu Val Asn
1               5                   10                  15

Ala Leu Pro Gln Ala Gln Gly Gly Ala Ala Ala Ser Ala Lys Val
            20                  25                  30

Ser Gly Thr Arg Phe Val Ile Asp Gly Lys Thr Gly Tyr Phe Ala Gly
            35                  40                  45

Thr Asn Ser Tyr Trp Ile Gly Phe Leu Thr Asn Asn Arg Asp Val Asp
        50                  55                  60

Thr Thr Leu Asp His Ile Ala Ser Ser Gly Leu Lys Ile Leu Arg Val
65                  70                  75                  80

Trp Gly Phe Asn Asp Val Asn Asn Gln Pro Ser Gly Asn Thr Val Trp
                85                  90                  95

Phe Gln Arg Leu Ala Ser Ser Gly Ser Gln Ile Asn Thr Gly Pro Asn
                100                 105                 110

Gly Leu Gln Arg Leu Asp Tyr Leu Val Arg Ser Ala Glu Thr Arg Gly
            115                 120                 125

Ile Lys Leu Ile Ile Ala Leu Val Asn Tyr Trp Asp Asp Phe Gly Gly
130                 135                 140

Met Lys Ala Tyr Val Asn Ala Phe Gly Gly Thr Lys Glu Ser Trp Tyr
145                 150                 155                 160

Thr Asn Ala Arg Ala Gln Glu Gln Tyr Lys Arg Tyr Ile Gln Ala Val
            165                 170                 175

Val Ser Arg Tyr Val Asn Ser Pro Ala Ile Phe Ala Trp Glu Leu Ala
        180                 185                 190

Asn Glu Pro Arg Cys Lys Gly Cys Asn Thr Asn Val Ile Phe Asn Trp
        195                 200                 205

Ala Thr Gln Ile Ser Asp Tyr Ile Arg Ser Leu Asp Lys Asp His Leu
210                 215                 220

Ile Thr Leu Gly Asp Glu Gly Phe Gly Leu Pro Gly Gln Thr Thr Tyr
225                 230                 235                 240

Pro Tyr Gln Tyr Gly Glu Gly Thr Asp Phe Val Lys Asn Leu Gln Ile
            245                 250                 255

Lys Asn Leu Asp Phe Gly Thr Phe His Met Tyr Pro Gly His Trp Gly
            260                 265                 270

Val Pro Thr Ser Phe Gly Pro Gly Trp Ile Lys Asp His Ala Ala Ala
        275                 280                 285

Cys Arg Ala Ala Gly Lys Pro Cys Leu Leu Glu Glu Tyr Gly Tyr Glu
290                 295                 300

Ser Asp Arg Cys Asn Val Gln Lys Gly Trp Gln Gln Ala Ser Arg Glu
305                 310                 315                 320

Leu Ser Arg Asp Gly Met Ser Gly Asp Leu Phe Trp Gln Trp Gly Asp
            325                 330                 335

Gln Leu Ser Thr Gly Gln Thr His Asn Asp Gly Phe Thr Ile Tyr Tyr
        340                 345                 350

Gly Ser Ser Leu Ala Thr Cys Leu Val Thr Asp His Val Arg Ala Ile
        355                 360                 365

Asn Ala Leu Pro Ala
    370

<210> SEQ ID NO 14
<211> LENGTH: 469
<212> TYPE: PRT

<213> ORGANISM: Podospora anserina

<400> SEQUENCE: 14

```
Met Val Lys Leu Leu Asp Ile Gly Leu Phe Ala Leu Ala Leu Ala Ser
1               5                   10                  15

Ser Ala Val Ala Lys Pro Cys Lys Pro Arg Asp Gly Pro Val Thr Tyr
            20                  25                  30

Glu Ala Glu Asp Ala Ile Leu Thr Gly Thr Thr Val Asp Thr Ala Gln
        35                  40                  45

Val Gly Tyr Thr Gly Arg Gly Tyr Val Thr Gly Phe Asp Glu Gly Ser
    50                  55                  60

Asp Lys Ile Thr Phe Gln Ile Ser Ala Thr Thr Lys Leu Tyr Asp
65                  70                  75                  80

Leu Ser Ile Arg Tyr Ala Ala Ile Tyr Gly Asp Lys Arg Thr Asn Val
                85                  90                  95

Val Leu Asn Asn Gly Ala Val Ser Glu Val Phe Phe Pro Ala Gly Asp
            100                 105                 110

Ser Phe Thr Ser Val Ala Ala Gly Gln Val Leu Leu Asn Ala Gly Gln
        115                 120                 125

Asn Thr Ile Asp Ile Val Asn Asn Trp Gly Trp Tyr Leu Ile Asp Ser
    130                 135                 140

Ile Thr Leu Thr Pro Ser Ala Pro Arg Pro His Asp Ile Asn Pro
145                 150                 155                 160

Asn Leu Asn Asn Pro Asn Ala Asp Thr Asn Ala Lys Lys Leu Tyr Ser
                165                 170                 175

Tyr Leu Arg Ser Val Tyr Gly Asn Lys Ile Ile Ser Gly Gln Gln Glu
            180                 185                 190

Leu His His Ala Glu Trp Ile Arg Gln Gln Thr Gly Lys Thr Pro Ala
        195                 200                 205

Leu Val Ala Val Asp Leu Met Asp Tyr Ser Pro Ser Arg Val Glu Arg
    210                 215                 220

Gly Thr Thr Ser His Ala Val Glu Asp Ala Ile Ala His His Asn Ala
225                 230                 235                 240

Gly Gly Ile Val Ser Val Leu Trp His Trp Asn Ala Pro Val Gly Leu
                245                 250                 255

Tyr Asp Thr Glu Glu Asn Lys Trp Trp Ser Gly Phe Tyr Thr Arg Ala
            260                 265                 270

Thr Asp Phe Asp Ile Ala Ala Thr Leu Ala Asn Pro Gln Gly Ala Asn
        275                 280                 285

Tyr Thr Leu Leu Ile Arg Asp Ile Asp Ala Ile Ala Val Gln Leu Lys
    290                 295                 300

Arg Leu Glu Ala Ala Gly Val Pro Val Leu Trp Arg Pro Leu His Glu
305                 310                 315                 320

Ala Glu Gly Gly Trp Phe Trp Trp Gly Ala Lys Gly Pro Glu Pro Ala
                325                 330                 335

Lys Gln Leu Trp Asp Ile Leu Tyr Glu Arg Leu Thr Val His His Gly
            340                 345                 350

Leu Asp Asn Leu Ile Trp Val Trp Asn Ser Ile Leu Glu Asp Trp Tyr
        355                 360                 365

Pro Gly Asp Asp Thr Val Asp Ile Leu Ser Ala Asp Val Tyr Ala Gln
    370                 375                 380

Gly Asn Gly Pro Met Ser Thr Gln Tyr Asn Glu Leu Ile Ala Leu Gly
385                 390                 395                 400
```

```
Arg Asp Lys Lys Met Ile Ala Ala Ala Glu Val Gly Ala Ala Pro Leu
                405                 410                 415
Pro Gly Leu Leu Gln Ala Tyr Gln Ala Asn Trp Leu Trp Phe Ala Val
            420                 425                 430
Trp Gly Asp Asp Phe Ile Asn Asn Pro Ser Trp Asn Thr Val Ala Val
        435                 440                 445
Leu Asn Glu Ile Tyr Asn Ser Asp Tyr Val Leu Thr Leu Asp Glu Ile
    450                 455                 460
Gln Gly Trp Arg Ser
465

<210> SEQ ID NO 15
<211> LENGTH: 493
<212> TYPE: PRT
<213> ORGANISM: Trichoderma reesei

<400> SEQUENCE: 15

Met Ala Gly Lys Leu Ile Leu Ala Leu Ala Ser Leu Val Ser Leu
1               5                   10                  15
Ser Ile Gln Gln Asn Cys Ala Ala Leu Phe Gly Gln Cys Gly Gly Ile
            20                  25                  30
Gly Trp Ser Gly Thr Thr Cys Cys Val Ala Gly Ala Gln Cys Ser Phe
        35                  40                  45
Val Asn Asp Trp Tyr Ser Gln Cys Leu Ala Ser Thr Gly Gly Asn Pro
    50                  55                  60
Pro Asn Gly Thr Thr Ser Ser Ser Leu Val Ser Arg Thr Ser Ser Ala
65                  70                  75                  80
Ser Ser Ser Val Gly Ser Ser Pro Gly Gly Asn Ser Pro Thr Gly
                85                  90                  95
Ser Ala Ser Thr Tyr Thr Thr Thr Asp Thr Ala Thr Val Ala Pro His
            100                 105                 110
Ser Gln Ser Pro Tyr Pro Ser Ile Ala Ala Ser Ser Cys Gly Ser Trp
        115                 120                 125
Thr Leu Val Asp Asn Val Cys Cys Pro Ser Tyr Cys Ala Asn Asp Asp
    130                 135                 140
Thr Ser Glu Ser Cys Ser Gly Cys Gly Thr Cys Thr Thr Pro Pro Ser
145                 150                 155                 160
Ala Asp Cys Lys Ser Gly Thr Met Tyr Pro Glu Val His His Val Ser
                165                 170                 175
Ser Asn Glu Ser Trp His Tyr Ser Arg Ser Thr His Phe Gly Leu Thr
            180                 185                 190
Ser Gly Gly Ala Cys Gly Phe Gly Leu Tyr Gly Leu Cys Thr Lys Gly
        195                 200                 205
Ser Val Thr Ala Ser Trp Thr Asp Pro Met Leu Gly Ala Thr Cys Asp
    210                 215                 220
Ala Phe Cys Thr Ala Tyr Pro Leu Leu Cys Lys Asp Pro Thr Gly Thr
225                 230                 235                 240
Thr Leu Arg Gly Asn Phe Ala Ala Pro Asn Gly Asp Tyr Tyr Thr Gln
                245                 250                 255
Phe Trp Ser Ser Leu Pro Gly Ala Leu Asp Asn Tyr Leu Ser Cys Gly
            260                 265                 270
Glu Cys Ile Glu Leu Ile Gln Thr Lys Pro Asp Gly Thr Asp Tyr Ala
        275                 280                 285
Val Gly Glu Ala Gly Tyr Thr Asp Pro Ile Thr Leu Glu Ile Val Asp
    290                 295                 300
```

-continued

```
Ser Cys Pro Cys Ser Ala Asn Ser Lys Trp Cys Cys Gly Pro Gly Ala
305                 310                 315                 320

Asp His Cys Gly Glu Ile Asp Phe Lys Tyr Gly Cys Pro Leu Pro Ala
                325                 330                 335

Asp Ser Ile His Leu Asp Leu Ser Asp Ile Ala Met Gly Arg Leu Gln
            340                 345                 350

Gly Asn Gly Ser Leu Thr Asn Gly Val Ile Pro Thr Arg Tyr Arg Arg
        355                 360                 365

Val Gln Cys Pro Lys Val Gly Asn Ala Tyr Ile Trp Leu Arg Asn Gly
    370                 375                 380

Gly Gly Pro Tyr Tyr Phe Ala Leu Thr Ala Val Asn Thr Asn Gly Pro
385                 390                 395                 400

Gly Ser Val Thr Lys Ile Glu Ile Lys Gly Ala Asp Thr Asp Asn Trp
            405                 410                 415

Val Ala Leu Val His Asp Pro Asn Tyr Thr Ser Ser Arg Pro Gln Glu
            420                 425                 430

Arg Tyr Gly Ser Trp Val Ile Pro Gln Gly Ser Gly Pro Phe Asn Leu
        435                 440                 445

Pro Val Gly Ile Arg Leu Thr Ser Pro Thr Gly Glu Gln Ile Val Asn
    450                 455                 460

Glu Gln Ala Ile Lys Thr Phe Thr Pro Pro Ala Thr Gly Asp Pro Asn
465                 470                 475                 480

Phe Tyr Tyr Ile Asp Ile Gly Val Gln Phe Ser Gln Asn
            485                 490
```